United States Patent [19]
Chang et al.

[11] Patent Number: 6,090,841
[45] Date of Patent: Jul. 18, 2000

[54] SUBSTITUTED PYRROLE DERIVATIVES AS CELL ADHESION INHIBITORS

[75] Inventors: Linda Chang, Wayne; Malcolm MacCoss, Freehold; William K. Hagmann, Westfield, all of N.J.

[73] Assignee: Merck & Co., Inc., Rahway, N.J.

[21] Appl. No.: 09/189,008

[22] Filed: Nov. 9, 1998

Related U.S. Application Data

[60] Provisional application No. 60/066,366, Nov. 21, 1997.

[51] Int. Cl.$^7$ .............................. A01N 43/36; C07F 9/32; C07D 207/32
[52] U.S. Cl. .......................... 514/423; 548/412; 548/537
[58] Field of Search ................................... 548/412, 537; 514/423

[56] References Cited

U.S. PATENT DOCUMENTS

| | | | |
|---|---|---|---|
| 5,510,332 | 4/1996 | Kogan et al. | 514/14 |
| 5,605,925 | 2/1997 | Martin et al. | 514/423 |

FOREIGN PATENT DOCUMENTS

| | | |
|---|---|---|
| WO 95/12611 | 5/1995 | WIPO . |
| WO 95/15973 | 6/1995 | WIPO . |
| WO 96/01644 | 1/1996 | WIPO . |
| WO 96/06108 | 2/1996 | WIPO . |
| WO 96/20216 | 7/1996 | WIPO . |
| WO 96/22966 | 8/1996 | WIPO . |
| WO 96/31206 | 10/1996 | WIPO . |
| WO 96/40781 | 12/1996 | WIPO . |
| WO 97/02289 | 1/1997 | WIPO . |
| WO 97/03094 | 1/1997 | WIPO . |

OTHER PUBLICATIONS

Schroff, Hitesh N., et als. Bioorganic & Medicinal Chemistry Letters vol. 6, No. 21 pp. 2495–2500 (1996).
Jackson, David Y. et als. Med. Chem., 40 pp. 3359–3368 (1997).
Artico, et al., Pyrryl Aryl Sulfones. Arch Pharm., vol. 328, No. 3, pp. 223–229, 1995.

*Primary Examiner*—Gary Geist
*Assistant Examiner*—Dominic Keating
*Attorney, Agent, or Firm*—Mollie M. Yang; David L. Rose

[57] ABSTRACT

Substituted pyrrole derivatives of Formula I are antagonists of VLA-4 and/or $\alpha_4\beta_7$, and as such are useful in the inhibition or prevention of cell adhesion and cell-adhesion mediated pathologies. These compounds may be formulated into pharmaceutical compositions and are suitable for use in the treatment of asthma, allergies, inflammation, multiple sclerosis, and other inflammatory and autoimmune disorders.

19 Claims, No Drawings

SUBSTITUTED PYRROLE DERIVATIVES AS CELL ADHESION INHIBITORS

CROSS REFERENCE TO RELATED APPLICATION

This application is based on, and claims priority from, provisional application No. 60/066,366 filed Nov. 21, 1997, which is hereby incorporated by reference in its entirety.

BACKGROUND OF THE INVENTION

The present invention relates to novel substituted pyrrole derivatives which are useful for the inhibition and prevention of leukocyte adhesion and leukocyte adhesion-mediated pathologies. This invention also relates to compositions containing such compounds and methods of treatment using such compounds.

Many physiological processes require that cells come into close contact with other cells and/or extracellular matrix. Such adhesion events may be required for cell activation, migration, proliferation and differentiation. Cell-cell and cell-matrix interactions are mediated through several families of cell adhesion molecules (CAMs) including the selectins, integrins, cadherins and immunoglobulins. CAMs play an essential role in both normal and pathophysiological processes. Therefore, the targetting of specific and relevant CAMs in certain disease conditions without interfering with normal cellular functions is essential for an effective and safe therapeutic agent that inhibits cell-cell and cell-matrix interactions.

The integrin superfamily is made up of structurally and functionally related glycoproteins consisting of $\alpha$ and $\beta$ heterodimeric, transmembrane receptor molecules found in various combinations on nearly every mammalian cell type. (for reviews see: E. C. Butcher, Cell, 67, 1033 (1991); T. A. Springer, Cell, 76, 301 (1994); D. Cox et al., "The Pharmacology of the Integrins." Medicinal Research Rev. 14, 195 (1994) and V. W. Engleman et al., "Cell Adhesion Integrins as Pharmaceutical Targets." in Ann. Repts. in Medicinal Chemistry, Vol. 31, J. A. Bristol, Ed.; Acad. Press, N.Y., 1996, p. 191).

VLA-4 ("very late antigen-4"; CD49d/CD29; or $\alpha_4\beta_1$) is an integrin expressed on all leukocytes, except platelets and mature neutrophils, including dendritic cells and macrophage-like cells and is a key mediator of the cell-cell and cell-matrix interactions of of these cell types (see M. E. Hemler, "VLA Proteins in the Integrin Family: Structures, Functions, and Their Role on Leukocytes." Ann. Rev. Immunol. 8, 365 (1990)). The ligands for VLA-4 include vascular cell adhesion molecule-1 (VCAM-1) and the CS-1 domain of fibronectin (FN). VCAM-1 is a member of the Ig superfamily and is expressed in vivo on endothelial cells at sites of inflammation. (See R. Lobb et al. "Vascular Cell Adhesion Molecule 1." in Cellular and Molecular Mechanisms of Inflammation, C. G. Cochrane and M. A. Gimbrone, Eds.; Acad. Press, San Diego, 1993, p. 151.) VCAM-1 is produced by vascular endothelial cells in response to proinflammatory cytokines (See A. J. H. Gearing and W. Newman, "Circulating adhesion molecules in disease.", Immunol. Today, 14, 506 (1993). The CS-1 domain is a 25 amino acid sequence that arises by alternative splicing within a region of fibronectin. (For a review, see R. O. Hynes "Fibronectins.", Springer-Velag, N.Y., 1990.) A role for VLA-4/CS-1 interactions in inflammatory conditions has been proposed (see M. J. Elices, "The integrin $\alpha_4\beta_1$ (VLA-4) as a therapeutic target" in Cell Adhesion and Human Disease, Ciba Found. Symp., John Wiley & Sons, N.Y., 1995, p. 79).

$\alpha_4\beta_7$ (also referred to as LPAM-1 and $\alpha_4\beta_p$) is an integrin expressed on leukocytes and is a key mediator of leukocyte trafficking and homing in the gastrointestinal tract (see C. M. Parker et al., Proc. Natl. Acad. Sci. USA, 89, 1924 (1992)). The ligands for $\alpha_4\beta_7$ include mucosal addressing cell adhesion molecule-1 (MadCAM-1) and, upon activation of $\alpha_4\beta_7$, VCAM-1 and fibronectin (Fn). MadCAM-1 is a member of the Ig superfamily and is expressed in vivo on endothelial cells of gut-associated mucosal tissues of the small and large intestine ("Peyer's Patches") and lactating mammary glands. (See M. J. Briskin et al., Nature, 363, 461 (1993); A. Hamann et al., J. Immunol., 152, 3282 (1994)). MadCAM-1 can be induced in vitro by proinflammatory stimuli (See E. E. Sikorski et al. J. Immunol., 151, 5239 (1993)). MadCAM-1 is selectively expressed at sites of lymphocyte extravasation and specifically binds to the integrin, $\alpha_4\beta_7$.

Neutralizing anti-$\alpha_4$ antibodies or blocking peptides that inhibit the interaction between VLA-4 and/or $\alpha_4\beta_7$ and their ligands have proven efficacious both prophylactically and therapeutically in several animal models of disease, including i) experimental allergic encephalomyelitis, a model of neuronal demyelination resembling multiple sclerosis (for example, see T. Yednock et al., "Prevention of experimental autoimmune encephalomyelitis by antibodies against $\alpha_4\beta_1$ integrin." Nature, 356, 63 (1993) and E. Keszthelyi et al., "Evidence for a prolonged role of $\alpha_4$ integrin throughout active experimental allergic encephalomyelitis." Neurology, 47, 1053 (1996)); ii) bronchial hyperresponsiveness in sheep and guinea pigs as models for the various phases of asthma (for example, see W. M. Abraham et al., "$\alpha_4$-Integrins mediate antigen-induced late bronchial responses and prolonged airway hyperresponsiveness in sheep." J. Clin. Invest. 93, 776 (1993) and A. A. Y. Mine and P. P. Piper, "Role of VLA-4 integrin in leucocyte recruitment and bronchial hyperresponsiveness in the gunea-pig." Eur. J. Pharmacol., 282 243 (1995)); iii) adjuvant-induced arthritis in rats as a model of inflammatory arthritis (see C. Barbadillo et al., "Anti-VLA-4 mAb prevents adjuvant arthritis in Lewis rats." Arthr. Rheuma. (Suppl.), 36 95 (1993) and D. Seiffge, "Protective effects of monoclonal antibody to VLA-4 on leukocyte adhesion and course of disease in adjuvant arthritis in rats." J. Rheumatol., 23, 12 (1996)); iv) adoptive autoimmune diabetes in the NOD mouse (see J. L. Baron et al., "The pathogenesis of adoptive murine autoimmune diabetes requires an interaction between $\alpha_4$-integrins and vascular cell adhesion molecule-1.", J. Clin. Invest., 93, 1700 (1994), A. Jakubowski et al., "Vascular cell adhesion molecule-Ig fusion protein selectively targets activated $\alpha$4-integrin receptors in vivo: Inhibition of autoimmune diabetes in an adoptive transfer model in nonobese diabetic mice." J. Immunol., 155, 938 (1995), and X. D. Yang et al., "Involvement of beta 7 integrin and mucosal addressin cell adhesion molecule-1 (MadCAM-1) in the development of diabetes in nonobese diabetic mice", Diabetes, 46, 1542 (1997)); v) cardiac allograft survival in mice as a model of organ transplantation (see M. Isobe et al., "Effect of anti-VCAM-1 and anti-VLA-4 monoclonal antibodies on cardiac allograft survival and response to soluble antigens in mice.", Tranplant, Proc., 26, 867 (1994) and S. Molossi et al., "Blockade of very late antigen-4 integrin binding to fibronectin with connecting segment-1 peptide reduces accelerated coronary arteriopathy in rabbit cardiac allografts." J. Clin Invest., 95, 2601 (1995)); vi) spontaneous chronic colitis in cotton-top tamarins which resembles human ulcerative colitis, a form of inflammatory bowel disease (see D. K. Podolsky et al., "Attenuation of colitis in the Cotton-top tamarin by anti-$\alpha_4$ integrin monoclonal antibody.", *J. Clin. Invest.*, 92, 372 (1993)); vii) contact hypersensitivity models as a model for skin allergic reactions (see T. A. Ferguson and T. S. Kupper, "Antigen-independent processes in antigen-specific immunity.", *J. Immunol.*, 150, 1172 (1993) and P. L. Chisholm et al., "Monoclonal antibodies to the integrin α-4 subunit inhibit the murine contact hypersensitivity response." *Eur. J. Immunol.*, 23, 682 (1993)); viii) acute neurotodic nephritis (see M. S. Mulligan et al., "Requirements for leukocyte adhesion molecules in nephrotoxic nephritis.", *J. Clin. Invest.*, 91, 577 (1993)); ix) tumor metastasis (for examples, see M. Edward, "Integrins and other adhesion molecules involved in melanocytic tumor progression.", *Curr. Opin. Oncol.*, 7, 185 (1995)); x) experimental autoimmune thyroiditis (see R. W. McMurray et al., "The role of α4 integrin and intercellular adhesion molecule-1 (ICAM-1) in murine experimental autoimmune thyroiditis." *Autoimmunity*, 23, 9 (1996); and xi) ischemic tissue damage following arterial occlusion in rats (see F. Squadrito et al., "Leukocyte integrin very late antigen4/vascular cell adhesion molecule-1 adhesion pathway in splanchnic artery occlusion shock." *Eur. J. Pharmacol.*, 318, 153 (1996; xii) inhibition of TH2 T-cell cytokine production including IL-4 and IL-5 by VLA-4 antibodies which would attenuate allergic responses (J.Clinical Investigation 100, 3083 (1997). The primary mechanism of action of such antibodies appears to be the inhibition of lymphocyte and monocyte interactions with CAMs associated with components of the extracellular matrix, thereby limiting leukocyte migration to extravascular sites of injury or inflammation and/or limiting the priming and/or activation of leukocytes.

There is additional evidence supporting a possible role for VLA-4 interactions in other diseases, including rheumatoid arthritis; various melanomas, carcinomas, and sarcomas; inflammatory lung disorders; acute respiratory distress syndrome (ARDS); atherosclerotic plaque formation; restenosis; uveitis and circulatory shock (for examples, see A. A. Postigo et al., "The $\alpha_4\beta_1$/VCAM-1 adhesion pathway in physiology and disease.", *Res. Immunol*, 144, 723 (1994) and J.-X. Gao and A. C. Issekutz, "Expression of VCAM-1 and VLA-4 dependent T-lymphocyte adhesion to dermal fibroblasts stimulated with proinflammatory cytokines." *Immunol.* 89, 375 (1996)).

At present, there is a humanized monoclonal antibody (Antegren® Athena Neurosciences/Elan ) against VLA-4 in clinical development for the treatment of "flares" associated with multiple sclerosis and a humanized monoclonal antibody (ACT-1®/LDP-02 LeukoSite) against $\alpha_4\beta_7$ in clinical development for the treatment of inflammatory bowel disease. Several peptidyl antagonists of VLA-4 have been described (D. Y. Jackson et al., "Potent α4β1 peptide antagonists as potential anti-inflammatory agents", *J. Med. Chem.*, 40, 3359 (1997); H. N. Shroff et al., "Small peptide inhibitors of α4β7 mediated MadCAM-1 adhesion to lymphocytes", *Bioorg. Med. Chem. Lett.*, 6, 2495 (1996); U.S. Pat. No. 5,510,332, WO97/03094, WO97/02289, WO96/40781, WO96/22966, WO96/20216, WO096/01644, WO96/06108, WO95/15973). There is one report of non-peptidyl inhibitors of the ligands for $\alpha_4$-integrins (WO96/31206). There still remains a need for low molecular weight, specific inhibitors of VLA-4- and α4β7-dependent cell adhesion that have improved pharmacokinetic and pharmacodynamic properties such as oral bioavailability and significant duration of action. Such compounds would prove to be useful for the treatment, prevention or suppression of various pathologies mediated by VLA-4 and α4β7 binding and cell adhesion and activation.

SUMMARY OF THE INVENTION

The compounds of the present invention are antagonists of the VLA-4 integrin ("very late antigen-4"; CD49d/CD29; or $\alpha_4\beta_1$) and/or the α4β7 integrin (LPAM-1 and $\alpha 4\beta_p$), thereby blocking the binding of VLA-4 to its various ligands, such as VCAM-1 and regions of fibronectin and/or α4β7 to its various ligands, such as MadCAM-1, VCAM-1 and fibronectin. Thus, these antagonists are useful in inhibiting cell adhesion processes including cell activation, migration, proliferation and differentiation. These antagonists are useful in the treatment, prevention and suppression of diseases mediated by VLA-4 and/or α4β7 binding and cell adhesion and activation, such as multiple sclerosis, asthma, allergic rhinitis, allergic conjunctivitis, inflammatory lung diseases, rheumatoid arthritis, septic arthritis, type I diabetes, organ transplantation, restenosis, autologous bone marrow transplantation, inflammatory sequelae of viral infections, myocarditis, inflammatory bowel disease including ulcerative colitis and Crohn's disease, certain types of toxic and immune-based nephritis, contact dermal hypersensitivity, psoriasis, tumor metastasis, and atherosclerosis.

DETAILED DESCRIPTION OF THE INVENTION

The present invention provides novel compounds of Formula I

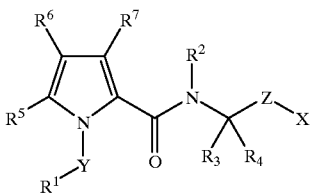

or a pharmaceutically acceptable salt thereof wherein:
X is 1) —C(O)OR$^d$,
  2) —P(O)(OR$^d$)(OR$^e$)
  3) —P(O)(R$^d$)(OR$^e$)
  4) —S(O)$_m$OR$^d$,
  5) —C(O)NR$^d$R$^h$, or
  6) -5-tetrazolyl;

Y is 1) —C(O)—,
  2) —O—C(O)—,
  3) —NR$^e$—C(O)—,
  4) —S(O)$_2$—,
  5) —P(O)(OR$^4$) or
  6) C(O)C(O);

Z is 1) a bond, or
  2) —C(R$^8$)(R$^9$)—;

R$^1$ is 1) C$_{1-10}$alkyl,
  2) C$_{2-10}$alkenyl,
  3) C$_{2-10}$alkynyl,
  4) Cy,
  5) Cy-C$_{1-10}$alkyl,
  6) Cy-C$_{2-10}$alkenyl,
  7) Cy-C$_{2-10}$alkynyl,
wherein alkyl, alkenyl, and alkynyl are optionally substituted with one to four substituents independently selected from R$^a$; and Cy is optionally substituted with one to four substituents independently selected from R$^b$;

R$^2$ is 1) hydrogen,

2) $C_{1-10}$alkyl,
3) Cy,
4) Cy-$C_{1-10}$alkyl, wherein alkyl is optionally substituted with one to four substituents independently selected from $R^a$; and Cy is optionally substituted with one to four substituents independently selected from $R^b$;

$R^3$ is 1) hydrogen,
2) $C_{1-10}$alkyl,
3) $C_{2-10}$alkenyl,
4) $C_{2-10}$alkynyl,
5) Cy-(Cy)$_p$,
6) Cy-(Cy)$_p$-$C_{1-10}$alkyl,
7) Cy-(Cy)$_p$-$C_{2-10}$alkenyl,
8) Cy-(Cy)$_p$-$C_{2-10}$alkynyl, alkyl, alkenyl and alkynyl are optionally substituted with one to four substituents independently selected from $R^a$; and Cy is optionally substituted with one to four substituents independently selected from $R^b$;

$R^4$ is 1) hydrogen,
2) $C_{1-10}$alkyl,
3) $C_{2-10}$alkenyl,
4) $C_{2-10}$alknyl,
5) Cy,
6) Cy-$C_{1-10}$alkyl, wherein alkyl, alkenyl and alkynyl are optionally substituted with one to four substituents selected from $R^a$, and Cy is optionally substituted with one to four substituents independently selected from $R^b$;

$R^5$, $R^6$, and $R^7$ are each independently
1) hydrogen, or
2) a group selected from $R^b$; or $R^5$ and $R^6$ or $R^6$ and $R^7$ and the two adjacent carbon atoms to which they are attached, together form a 5-7 membered saturated or unsaturated monocyclic ring containing zero to two heteroatoms selected from N, O or S;

$R^8$ is 1) hydrogen,
2) a group selected from $R^a$, or
3) a group selected from $R^1$;

$R^9$ is 1) hydrogen,
2) $C_{1-10}$alkyl,
3) $C_{2-10}$alkenyl,
4) $C_{2-10}$alkynyl,
5) Cy,
6) Cy-$C_{1-10}$alkyl, wherein alkyl, alkenyl and alkynyl are optionally substituted with one to four substituents selected from $R^a$, and Cy is optionally substituted with one to four substituents independently selected from $R^b$.

$R^a$ is 1) —$CF_3$;
2) —$OR^d$,
3) —$NO_2$,
4) halogen
5) —$S(O)_m R^d$,
6) —$SR^d$,
7) —$S(O)_2 OR^d$,
8) —$S(O)_m NR^d R^e$,
9) —$NR^d R^e$,
10) —$O(CR^f R^g)_n NR^d R^e$,
11) —$C(O)R^d$,
12) —$CO_2 R^d$,
13) —$CO_2(CR^f R^g)_n CONR^d R^e$,
14) —$OC(O)R^d$,
15) —CN,
16) —$C(O)NR^d R^e$,
17) —$NR^d C(O)R^e$,
18) —$OC(O)NR^d R^e$,
19) —$NR^d C(O)OR^e$, or
20) —$NR^d C(O)NR^d R^e$;
21) —$CR^d(N—OR^e)$, or
22) Cy optionally substituted with a group independently selected from $R^c$;

$R^b$ is 1) a group selected from $R^a$,
2) $C_{1-10}$alkyl,
3) $C_{2-10}$alkenyl,
4) $C_{2-10}$alkynyl, or
5) Cy-$C_{1-10}$alkyl, wherein alkyl, alkenyl, alkynyl, and Cy are optionally substituted with a group independently selected from $R^c$; substituted with a group independently selected from $R^c$;

$R^c$ is 1) halogen,
2) amino,
3) carboxy,
4) $C_{1-4}$alkyl,
5) $C_{1-4}$alkoxy,
6) aryl,
7) aryl $C_{1-4}$alkyl, or
8) aryloxy;

$R^d$ and $R^e$ are independently selected from the group consisting of
1) hydrogen,
2) $C_{1-10}$alkyl,
3) $C_{2-10}$alkenyl,
4) $C_{2-10}$alkynyl,
5) Cy, and
6) Cy $C_{1-10}$alkyl, wherein alkyl, alkenyl, alkynyl and Cy is optionally substituted with one to four substituents independently selected from $R^c$; or $R^d$ and $R^e$ together with the atoms to which they are attached form a heterocyclic ring of 5 to 7 members containing 0–2 additional heteroatoms independently selected from oxygen, sulfur and nitrogen;

$R^f$ and $R^g$ are independently selected from hydrogen, $C_{1-10}$alkyl, Cy and Cy $C_{1-10}$alkyl; or $R^f$ and $R^g$ together with the carbon to which they are attached form a ring of 5 to 7 members containing 0–2 heteroatoms independently selected from oxygen, sulfur and nitrogen;

$R^h$ is 1) hydrogen,
2) $C_{1-10}$alkyl,
3) $C_{2-10}$alkenyl,
4) $C_{2-10}$alkyl,
5) cyano,
6) aryl,
7) aryl $C_{1-10}$alkyl,
8) heteroaryl,
9) heteroaryl $C_{1-10}$alkyl, or
10) —$SO_2 R^i$;

wherein alkyl, alkenyl, and alkynyl are optionally substituted with one to four substituents independently selected from $R^a$; and aryl and heteroaryl are each optionally substituted with one to four substituents independently selected from $R^b$;

$R^i$ 1) $C_{1-10}$alkyl
2) $C_{2-10}$alkenyl,
3) $C_{2-10}$alkynyl, or
4) aryl;

wherein alkyl, alkenyl, alkynyl and aryl are each optionally substituted with one to four substituents independently selected from $R^c$;

Cy is cycloalkyl, heterocyclyl, aryl, or heteroaryl;

m is an integer from 1 to 2;

n is an integer from 1 to 10; and p is 0 or 1.

In one subset of compounds of formula I $R^1$ is Cy or Cy-$C_{1-10}$alkyl where Cy and alkyl are optionally substituted as provided above. For the purpose of $R^1$, Cy is preferably aryl optionally substituted with one or two groups selected from $R^b$.

In another subset of compounds of formula I Y is —C(O)— or $SO_2$.

In another subset of compounds of formula I X is —C(O)OR$^d$.

A preferred embodiment of compound of formula I are compounds of formula Ia:

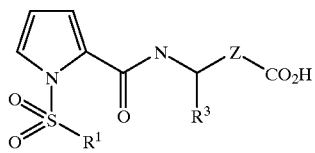

Ia wherein $R^1$ is aryl optionally substituted with one or two groups independnetly selected from $R^b$;

$R^3$ is 1) $C_{1-10}$alkyl,
2) Cy-(Cy)$_p$, or
3) Cy-(Cy)$_p$-$C_{1-10}$alkyl, wherein alkyl is optionally substituted with one to four substituents independently selected from $R^a$; and Cy is optionally substituted with one to four substituents independently selected from $R^b$;

Z is 1) a bond, or
2) —CH$_2$—; and the other variables are as provided under formula I.

Representative compounds of formula I are as follows:

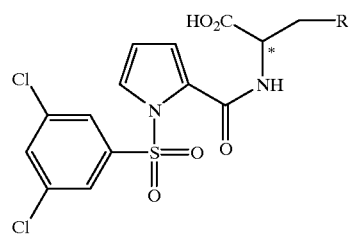

| Ex. No. | R |
|---|---|
| 1 | phenyl |
| 2 | benzyl |
| 3 | propyl |
| 4 | 4-(t-butoxyphenyl) |
| 5 | 4-(benzyloxy)phenyl |
| 6 | 4-(2-methoxyphenyl)phenyl |
| 7 | 4-(3-methoxyphenyl)phenyl |
| 8 | 4-(2-cyanophenyl)phenyl |
| 9 | 4-(3-cyanophenyl)phenyl |
| 10 | 4-(2-propyloxyphenyl)phenyl |
| 11 | 4-( 2-tetrazolylphenyl)phenyl |
| 12 | 4-(2-methylthiophenyl)phenyl |
| 13 | 4-(2-methylsulfonylphenyl)phenyl |
| 14 | 4-hydroxyphenyl |

-continued

| Ex. No. | R |
|---|---|

* stereoconfiguration is that of an L-amino acid

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon—carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon—carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic saturated carbocyclic rings, each of which having from 3 to 10 carbon atoms. The term also inccludes monocyclic ring fused to an aryl group in which the point of attachment is on the non-aromatic portion. Examples of cycloalkyl include cyclopropyl, cyclopentyl, cyclohexyl, cycloheptyl, tetrahydronaphthyl, decahydronaphthyl, indanyl, and the like.

"Aryl" means mono- or bicyclic aromatic rings containing only carbon atoms. The term also includes aryl group fused to a monocyclic cycloalkyl or monocyclic heterocyclyl group in which the point of attachment is on the aromatic portion. Examples of aryl include phenyl, naphthyl, indanyl, indenyl, tetrahydronaphthyl, 2,3-dihydrobenzofuranyl, benzopyranyl, 1,4-benzodioxanyl, and the like.

"Heteroaryl" means a mono- or bicyclic aromatic ring containing at least one heteroatom selected from N, O and S, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

"Heterocyclyl" means mono- or bicyclic saturated rings containing at least one heteroatom selected from N, S and O, each of said ring having from 3 to 10 atoms. The term also includes monocyclic heterocycle fused to an aryl or heteroaryl group in which the point of attachment is on the non-aromatic portion. Examples of "heterocyclyl" include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like.

"Halogen" includes fluorine, chlorine, bromine and iodine.

Optical Isomers—Diastereomers—Geometric Isomers—Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general Formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Utilities

The ability of the compounds of Formula I to antagonize the actions of VLA-4 and/or $\alpha 4\beta 7$ integrin makes them useful for preventing or reversing the symptoms, disorders or diseases induced by the binding of VLA-4 and or $\alpha 4\beta 7$ to their various respective ligands. Thus, these antagonists will inhibit cell adhesion processes including cell activation, migration, proliferation and differentiation. Accordingly, another aspect of the present invention provides a method for the treatment (including prevention, alleviation, amelioration or suppression) of diseases or disorders or symptoms mediated by VLA-4 and/or $\alpha 4\beta 7$ binding and cell adhesion and activation, which comprises administering to a mammal an effective amount of a compound of Formula I. Such diseases, disorders, conditions or symptoms are for example (1) multiple sclerosis, (2) asthma, (3) allergic rhinitis, (4) allergic conjunctivitis, (5) inflammatory lung diseases, (6) rheumatoid arthritis, (7) septic arthritis, (8) type I diabetes, (9) organ transplantation rejection, (10) restenosis, (11) autologous bone marrow transplantation, (12) inflammatory sequelae of viral infections, (13) myocarditis, (14) inflammatory bowel disease including ulcerative colitis and Crohn's disease, (15) certain types of toxic and immune-based nephritis, (16) contact dermal hypersensitivity, (17) psoriasis, (18) tumor metastasis, (19) hepatitis, and (20) atherosclerosis.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

Pharmaceutical Compositions

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula I | 25 |
| Microcrystalline Cellulose | 415 |
| Povidone | 14.0 |
| Pregelatinized Starch | 3.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liquid Concentrate | 1.2 mg |
| Trichlorofluoromethane, NF | 4.025 g |
| Dichlorodifluoromethane, NF | 12.15 g |

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to: (a) other VLA-4 antagonists such as those described in U.S. Pat. No. 5,510,332, WO97/03094, WO97/02289, WO96/40781, WO96/22966, WO96/20216, WO96/01644, WO96/06108, WO95/15973, WO96/31206 and WO98/42656; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as $\beta 2$-agonists (terbutaline, metaproterenol, fenoterol, isoetharine, albuterol, bitolterol, salmeterol and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors such as celecoxib; (h) inhibitors of phosphodiesterase type IV (PDE-IV); (i) antagonists of the chemokine receptors, especially CCR-1, CCR-2, and CCR-3; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), $\alpha$-glucosidase inhibitors (acarbose) and glitazones (troglitazone, pioglitazone, englitazone, MCC-555, BRL49653 and the like); (l) preparations of interferon beta (interferon beta-1a, interferon beta-1b); (m) anticholinergic agents such as muscarinic antagonists (ipratropium bromide); (n) other compounds such as 5-aminosalicylic acid and prodrugs thereof, antimetabolites such as azathioprine and 6-mercaptopurine, and cytotoxic cancer chemotherapeutic agents.

The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

The compounds of Formula I may be prepared by several general synthetic methods as described in for example, *Principles of Pepetide Synthesis*, 2nd Ed., M. Bodanszky, Springer Verlag, Berlin Heidelberg, 1993. The compound of the present invention can be prepared by procedures illustrated in the accompanying schemes. In general, these compounds are constructed in such a way that the pyrrole nitrogen is elaborated before modifications are made to the pyrrole 2-carbonyl position.

Although the reaction schemes described below are reasonably general, it will be understood by those skilled in the art of organic synthesis that one or more functional groups present in a given compound of Formula I may render the molecule incompatible with a particular synthetic sequence. In such a case an alternative route, an altered order of steps, or a strategy of protection and deprotection may be employed. In all cases the particular reaction conditions (including reagents, solvent, temperature, and time) should be chosen so that they are consistent with the nature of the functionalities present in the molecule.

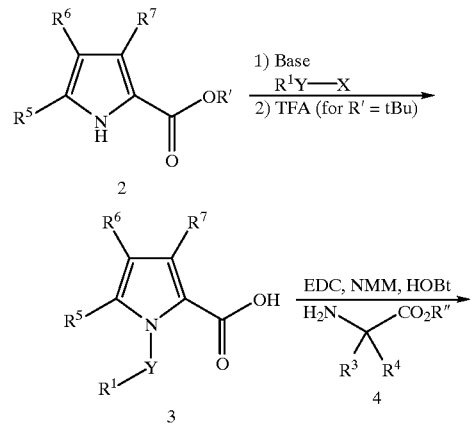

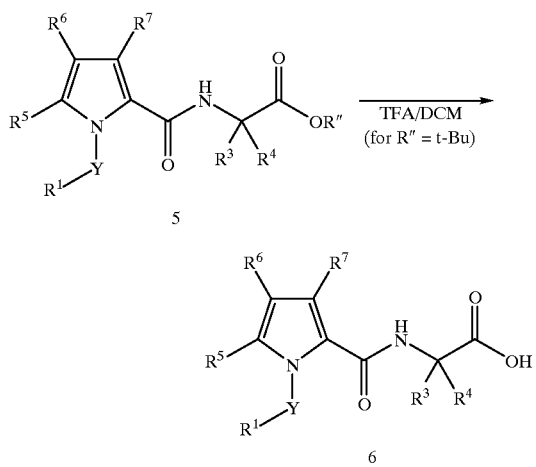

As shown in Scheme 1, a suitably substituted t-butyl pyrrole-2-carboxylate or equivalent (2, $CO_2R'$=t-butyl ester or another ester which does not require base to hydrolyze) is acylated or sulfonylated under phase transfer conditions based on an established method (see for example, Illi, V. O., *Synthesis*, 1979, 136; Anderson, H. J. et al., *Can. J. Chem.*, 63, 1985, 896; Yajima, H. et al., *Chem. Pharm. Bull.*, 32, 1984, 2660). The ester moiety is then hydrolyzed under appropriate non-basic conditions to provide 3. Compound 3 is then coupled with an appropriately elaborated amino acid ester 4 under suitable conditions to provide 5 which upon hydrolysis yields the target compound 6.

Scheme 2 addresses further elaborations at $R^3$ and/or $R^4$ of compound 6. The example shown is that for derivatizations on H-L-(OtBu)Tyr-(OR″) as 4. Starting with 5a, the free phenol is restored under standard conditions to provide the key intermediate 7. This compound can be further elaborated for example via alkylation or acylation to grant entry into a variety of functional groups. When the desired $R^d$ has been obtained, the ester is hydrolyzed to the acid to provide the desired targets 6a.

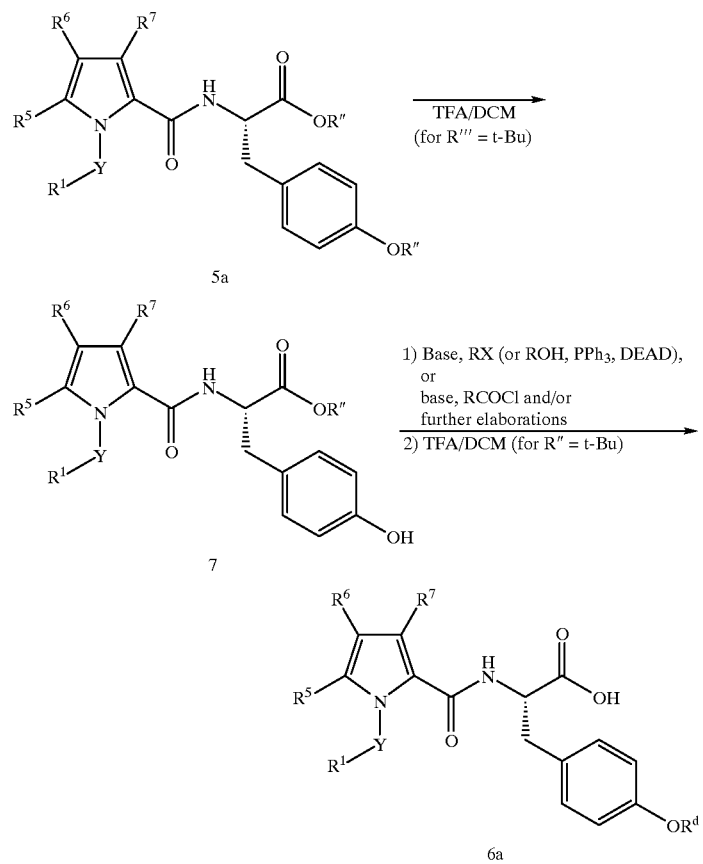

Scheme 2

Scheme 3 shows a route to elaborate $R^3$ and/or $R^4$ of Compound 6 via the 4-iodophenylalanine derivative 5b. As illustrated below, this compound can be used directly in a Pd(0) catalyzed coupling reaction with an appropriately substituted boronic acid to form the biaryl compound. Subsequent to any further desired elaborations to attain the desired $R^y$, the ester is hydrolyzed to give the target compounds 8. Some biaryl compounds are more accessible by the trimethylstannyl derivative 5c which can be prepared from 5b as indicated. Subsequent palladium(II) catalyzed coupling reaction of 5c with a suitably substituted bromo (or iodo) arene provides the biaryl species 9 which could be further elaborated if needed, to achieve the desired $R^y$. Hydrolysis of the ester gives the target compound 8.

At room temperature, to a solution of pyrrole-2-carboxylic acid (500 mg, 4,5 mmol) in anhydrous dichloromethane (5 mL) and anhydrous N,N-dimethylformamide (2.5 mL) was added anhydrous cyclohexane (20 mL). With vigorous stirring, to this clear solution was added (0.85 mL, 1.033 g, 4.73 mmol) of tert-butyl 2,2,2-trichloroacetimidate followed by dropwise addition of boron trifluoride diethyl etherate (170 mL). After stirring at room temperature for 2 hr, additional tert-butyl 2,2,2-trichloroacetimidate (0.85 mL, 1.033 g, 4.73 mmol) and boron trifluoride diethyl etherate (85 mL) were added to the reaction mixture. After stirring at room temperature for an additional 3 hr, additional tert-butyl 2,2,2-trichloroacetimidate (0.85 mL, 1.033 g, 4.73 mmol) and boron trifluoride diethyl etherate (85 mL) were added to

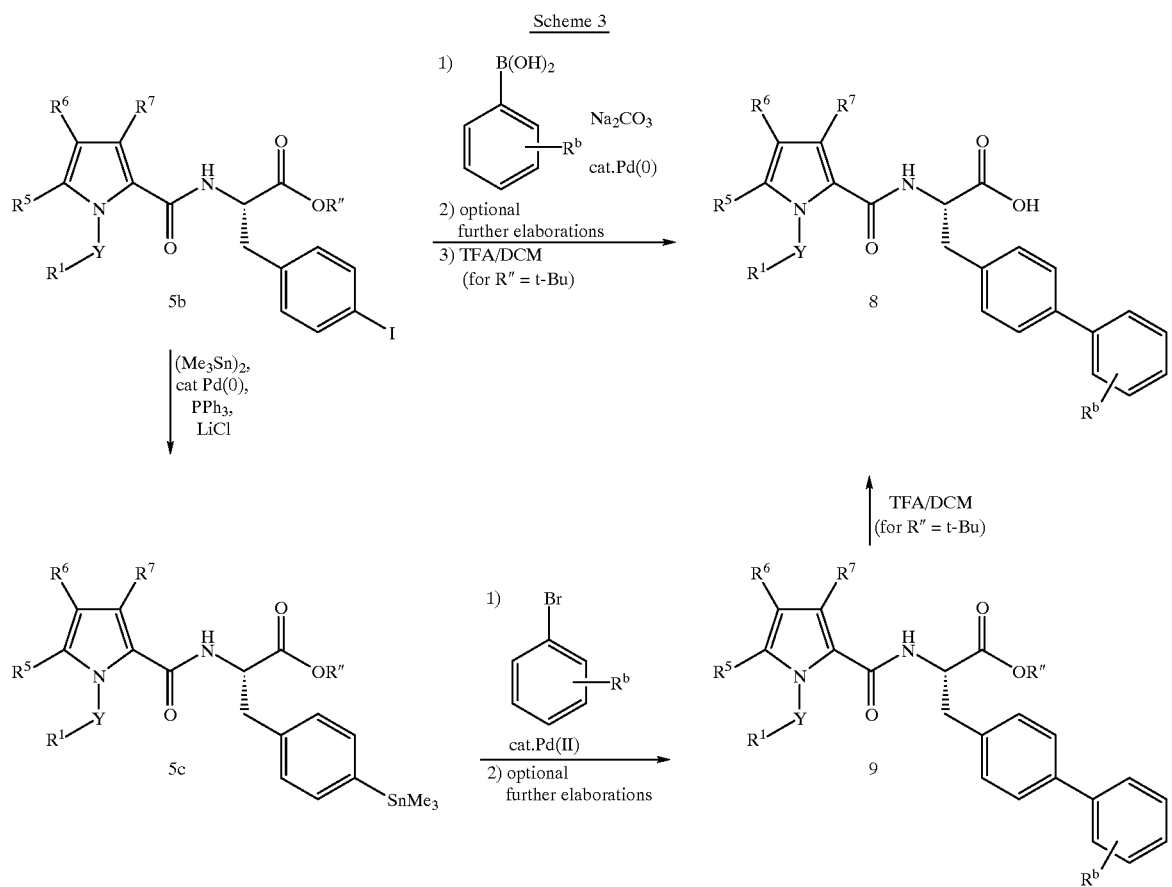

In the various synthetic methods described above, protection and deprotection of functional groups such as hydroxyl and amino groups may be required. The selection of the appropriate protecting groups, and methods for introducing and removing the protecting groups are within the knowledge of one skilled in the art, and are also described in standard reference books such as Greene and Wuts, *Protective Groups in Organic Synthesis*, 2d Ed., John Wiley & Sons, Inc., 1991.

The following examples illustrate the preparation of the compounds of Formula I and their incorporation into pharmaceutical compositions and as such are not to be construed as limiting the scope of the invention in any manner.

EXAMPLE 1

N-[N-(3,5-Dichlorobenzenesulfonyl)pyrrole-2-carbonyl]-(L)-phenylalanine

Step A: tert-Butyl pyrrole-2-carboxylate.

the reaction mixture. After stirring at room temperature overnight, the reaction mixture was filtered through a pad of celite, and the residue was washed with ether. The solvent was removed from the filtrate by rotoevaportation and the crude product was purified by flash column chromatography on silica gel eluted with 3–6% ethyl acetate in hexane to give the title compound as a white solid (600 mg, 80% yield), homogeneous by TLC (1/1 hexane/Ethyl acetate).

Mass spectrum (ESI) m/e=167.1 (M+1)$^+$; 300 MHz $^1$H NMR (CDCl$_3$) d 1.57 (s, 9 H), 6.22–6.25 (m, 1 H), 6.83–6.85 (m, 1 H), 6.90–6.92 (m, 1 H), 9.30 (br s, 1H).

Step B: tert-Butyl N-(3,5-dichlorobenzenesulfonyl)pyrrole-2-carboxylate

At room temperature, to a stirred solution of tert-butyl pyrrole-2-carboxylate (obtained from Step A) (120 mg, 0.718 mmol) dissolved in benzene (2.5 mL) was added tetra-N-butylammonium hydrogen sulfate (49 mg, 0.144 mmol) followed by 50% aqueous sodium hydroxide solution (0.72 mL). After 10 min, a solution of 3,5-dichlorobenzenesulfonyl chloride (264 mg, 1.08 mmol) dissolved in benzene (1 mL) was added dropwise via a gas-tight syringe over a 25 min period. The reaction mixture was allowed to stir overnight at room temperature. Ethyl acetate and water were added and the phases were separated. The aqueous layer was re-extracted twice with ethyl acetate and the combined organic layers were washed with water (3×) and dried over anhydrous sodium sulfate. The crude product obtained after filtration and removal of solvents by rotoevaporation was purified by flash column chromatography on silica gel eluted with 0.5–2.5% ethyl acetate in hexane to afford the title compound (104 mg), homogeneous by TLC in 10/1 hexane/ethyl acetate; 77% yield, based on starting material consumed) and recovered starting material (58 mg, 50%).

Mass spectrum (ESI) m/e=375.1 (M+1)$^+$; 300 MHz $^1$H NMR (CDCl$_3$) d 1.46 (s, 9 H), 6.32 (t, J=3.5 Hz, 1H), 6.95 (dd, J=3.5, 1.9 Hz, 1H), 7.57 (m, 1H), 7.60 (m, 1H), 7.85 (d, J=1.8, Hz, 1H).

Step C: N-(3,5-Dichlorobenzenesulfonyl)pyrrole-2-carboxylic acid

At 0° C., to a solution of tert-butyl (N-3,5-dichlorobenzenesulfonyl)-pyrrole 2-carboxylate (obtained from Step B) (88 mg, 0.234 mmol) dissolved in anhydrous dichloromethane (0.2 mL) was added dropwise a 1:1 solution of trifluoroacetic acid and dichloromethane solution (0.4 mL). After 3 minutes, the ice bath was removed and the pinkish reaction mixture was allowed to stirred at room temperature for 40 min. The excess trifluoroacetic acid was removed by a stream of nitrogen gas. The residue was dissolved in dichloromethane and methanol and evaporated under reduced pressure and pumped under high vacuum overnight at room temperature. The title compound was obtained (75 mg) as a white solid, homogeneous by TLC (10% methanol in dichloromethane ). This material was used without further purification in the subsequent reaction.

Mass spectrum (ESI) m/e=318.9 (M+1)$^+$; 300 MHz $^1$H NMR (CDCl$_3$) d 2.40 (br s, 1H), 6.37 (d, J=4.4 Hz, 1H), 7.16 (dd, J=3.6, 1.9 Hz, 1H), 7.56 (t, J=1.9 Hz, 1H), 7.70 (dd, J=3.3, 1.9 Hz, 1H), 7.80 (d, J=1.8 Hz, 2H).

Step D: N-[N-(3,5-Dichlorobenzenesulfonyl)pyrrole-2-carbonyl]-(L)-phenylalanine, tert-butyl ester.

At room temperature; to a solution of (N-3,5-dichlorobenzenesulfonyl)pyrrole-2-carboxylic acid (obtained from Step C) (40 mg, 0.125 mmol) in dimethylformamide (0.125 mL) was added 1-hydroxybenzotriazole hydrate (19 mg, 0.137 mmol), N-methylmorpholine (35 µL, 32 mg, 0.313 mmol), and (L)-phenylalanine, tert-butyl ester hydrochloride (39 mg, 0.15 mmol). Dimethylformamide was added as required to keep all components in solution. Subsequently, 1-(3-dimethylaminopropyl)3-ethylcarbodiimide hydrochloride (EDC; 29 mg, 0.15 mmol) was added and the reaction mixture was stirred at room temperature for 36 hr. Water was added and the organic layer was extracted with ethyl acetate (3×). The combined organic layers were washed with water (2×), saturated salt solution, and dried over anhydrous sodium sulfate. The solution was filtered and the solvents removed by rotoevaporation. The residue was purified by flash column chromatography on silica gel eluted with 3–6% ethyl acetate in hexane to afford the title compound (57 mg, 87% yield) as a foam, homogeneous by TLC in 4/1 hexane/ethyl acetate.

Mass spectrum (ESI) m/e=523.0 (M+1)$^+$; 400 MHz $^1$H NMR (CDCl$_3$) δ 1.41 (s, 9 H), 3.15 (d, J=5.0 Hz, 2H), 4.81 (dt, J=7.5, 5.6 Hz, 1H), 6.27 (t, J=3.4 Hz, 1H), 6.48 (d, J=7.6 Hz, 1H), 6.59 (dd, J=3.6, 1.7 Hz, 1H), 7.14–7.18 (m, 2H), 7.20–7.30 (m, 3H), 7.45 (dd, J=3.3, 1.7 Hz, 1H), 7.55 (t, J=1.8 Hz, 1H), 7.92 (d, J=1.8 Hz, 2H).

Step E: N-[N-(3,5-Dichlorobenzenesulfonyl)pyrrole-2-carbonyl]-(L)-phenylalanine

At 0° C., to a solution of N-[(N-3,5-dichlorobenznesulfonyl)pyrrole-2-carbonyl]-(L)-phenylalanine, tert-butyl ester (8.5 mg, 0.016 mmol) dissolved in anhydrous dichloromethane (50 µL) was added dropwise 0.085 mL of a 1:1 solution of trifluoroacetic acid/dichloromethane (85 µL). After stirring for 3 min, the ice bath was removed and the pinkish reaction mixture was stirred at room temperature for 2 hr. The excess trifluoroacetic acid was removed by a stream of nitrogen gas. The residue was taken up in dichloromethane and methanol and rotoevaporated and then pumped overnight under reduced pressure at room temperature. This crude product was purified by flash column chromatography on silica gel eluted with 2–9% methanol in dichloromethane to afford the title compound (6 mg, 80% yield) as a foam, homogeneous by TLC in 10% methanol in dichloromethane.

Mass spectrum (ESI) m/e=467.1 (M+1)$^+$; 500 MHz $^1$H NMR (CDl$_3$OD) δ 3.06 (dd, J=14, 8.4 Hz, 1 H), 3.26 (dd, J=14, 5.3 Hz, 1 H), 4.70 (dd, J=8.4, 5.3 Hz, 1H), 6,33 (t, J=3.5 Hz, 1H), 6.67 (dd, J=3.4, 1.6 Hz, 1H), 7.16–7.21 (m, 1H), 7.22–7.28 (m, 4H), 7.57 (dd, J=3.4, 1.8 Hz, 1H), 7.75 (t, J=1.9 Hz, 1H), 7.92 (d, J=1.8 Hz, 2H).

EXAMPLE 2

N-[N-(3,5-Dichlorobenznesulfonyl)pyrrole-2-carbonyl]-(L)-homophenylalanine

Step A: N-Carbobenzyloxy-(L)-homophenylalanine, tert-butyl ester

At room temperature, to a solution of (N-carbobenzyloxy)-(L)-homophenylalanine (0.476 g, 1.52 mmol) in anhydrous dichloromethane (3.5 mL) was added anhydrous cyclohexane (7 mL). To this clear solution was added with vigourous stirring tert-butyl 2,2,2-trichloroacetimidate (0.30 mL, 1.67 mmol) followed by dropwise addition of boron trifluoride diethyl etherate (30 mL). After stirring at room temperature for 2 hr, additional tert-butyl 2,2,2-trichloroacetimidate (0.45 mL, 2.50 mmol) and boron trifluoride diethyl etherate (45 mL) were added to the reaction mixture and stirring was continued overnight at room temperature. The reaction mixture was filtered through a pad of celite, and the residue was washed with ether. The solvent was removed from the filtrate by rotoevaporation and the crude product was purified by flash column chromatography on silica gel eluted with 2–6% ethyl acetate in hexane to afford the title compound (211 mg, 38% yield), homogeneous by TLC (4/1 hexane/ethyl acetate).

Mass spectrum (ESI) m/e=387(M+NH$_4$)$^+$; 400 MHz $^1$H NMR (CDCl$_3$) δ 1.46 (s, 9H), 1.85–2.00 (m, 1H), 2.08–2.20 (m, 1H), 2.56–2.73 (m, 2H), 4.28–4.35 (m, 1H), 5.33 (br d, 1H), 7.10–7.23 (m, 3H), 7.23–7.40 (m, 7 H).

Step B: (L)-Homophenylalanine, tert-butyl ester

A solution of (N-carbobenzyloxy)-(L)-homophenylalanine, tert-butyl ester (100 mg, 0.281 mmol) in anhydrous ethanol (2 mL) and anhydrous ethyl acetate (2 mL) was degassed and the reaction flask filled with hydrogen. 10% Palladium on carbon catalyst (25 mg) was added and the mixture was hydrogenated under a balloon of hydrogen at room temperature for 2.3 hr. The catalyst was removed by filtration through a pad of celite, and solvent was removed from the filtrate by rotoevaporation. After pumping under reduced pressure at room temperature, the material thus obtained (homogeneous by TLC in 4/1 hexane/ethyl acetate) was used in the subsequent reaction without further purification.

mass spectrum (ESI) m/e=222 (M+1)$^+$. 400 MHz $^1$H NMR (CD$_3$OD) δ 1.55 (s, 9H), 2.05–2.25 (m, 2H), 2.68–2.75 (m, 1H), 2.75–2.85 (m, 1H), 3.90(t, J=6.3 Hz, 1H), 7.22–7.25 (m, 3H), 7.25–7.33 (m, 2 H).

Step C: N-[N-(3,5-Dichlorobenznesulfonyl)pyrrole-2-carbonyl]-(L)-homophenylalanine The title compound was prepared in two steps from N-(3,5-dichlorobenzenesulfonyl)pyrrole-2-carboxylic acid (obtained from Example 1, Step C) and (L)-homophenylalanine, tert-butyl ester (obtained from Step B) as described in Example 1 Steps D and E. This provided the title compound in 67% yield (last step), homogeneous by TLC (10% methanol in dichloromethane).

mass spectrum (ESI) m/e=481.3 (M+1)$^+$; 400 MHz $^1$H NMR (CD$_3$OD) δ 2.05–2.12 (m, 1H), 2.18–2.25 (m, 1H), 2.68–2.85 (m, 2H), 4.45 (dd, J=7.0, 4.0 Hz, 1H), 6.40 (t, J=3.4 Hz, 1H), 6.84 (dd, J=3.6, 1.7 Hz, 1H), 7.12–7.20 (m, 1H), 7.21–7.27 (m, 4 H), 7.62 (dd, J=3.3, 1.7 Hz, 1H), 7.77 (t, J=1.8 Hz, 1H), 7.98 (d, J=1.9 Hz, 1H).

EXAMPLE 3

N-[N-(3,5-Dichlorobenzenesulfonyl)pyrrole-2-carbonyl]-(L)-norleucine

The title compound was prepared in 91% yield as described for N-[N-(3,5-dichlorobenznesulfonyl)pyrrole-2-carbonyl]-(L)-homophenylalanine in Example 2 except that (L)-norleucine, tert-butyl ester was used instead of (L)-homophenylalanine, tert-butyl ester. The title compound was homogeneous by TLC (10% methanol in dichloromethane).

Mass spectrum (ESI) m/e=433.1 (M+1)$^+$; 400 MHz $^1$H NMR (CD$_3$OD) δ 0.92 (t, J=7.1 Hz, 3H), 1.35–1.50 (m, 4H), 1.68–1.80 (m, 1H), 1.85–2.00 (m, 1H), 4.31 (dd, J=4.6, 3.8 Hz, 1H), 6.38 (t, J=3.4 Hz, 1H), 6.85 (dd, J=3.5, 1.7 Hz, 1H), 7.59 (dd, J=3.3, 1.7 Hz, 1H), 7.79 (t, J=1.8 Hz, 1H), 7.96 (d, J=1.8 Hz, 2H).

EXAMPLE 4

N-[N-(3,5-Dichlorobenznesulfonyl)pyrrole-2-carbonyl]-(L)-O-tert-butyl-tyrosine Step A: N-[N-(3,5-Dichlorobenznesulfonylpyrrole-2-carbonyl]-(L)-O-tert-butyl-tyrosine, methyl ester The title compound was prepared in 73% yield according to Example 1, Step D except that (L)-O-tert-butyl-tyrosine, methyl ester was used instead of (L)-phenylalanine, tert-butyl ester.

Mass spectrum (ESI) m/e=553.4 (M+1)$^+$; 400 MHz $^1$H NMR (CDCl$_3$) δ 1.30 (s, 9H), 3.10–3.20 (m, 2H), 3.72 (s, 3H), 4.88–4.95 (m, 1H), 6.26 (t, J=3.5 Hz, 1H), 6.40–6.45 (d, J=7.5 Hz, 1H), 6.56 (dd, J=3.5, 1.7 Hz, 1H), 6.89 (d, J=8.6 Hz, 2H), 6.98 (d, J=8.6 Hz, 2H), 7.44 (dd, J=3.3, 1.7 Hz, 1H), 7.56 (t, J=1.8 Hz, 1H), 7.91 (d, J=1.8 Hz, 2H).

Step B: N-[N-(3,5-Dichlorobenznesulfonyl)pyrrole-2-carbonyl]-(L)-O-tert-butyl-tyrosine At 0° C., to a solution of N-[N-(3,5-dichlorobenznesulfonyl)pyrrole-2-carbonyl]-(L)-O-tert-butyl-tyrosine, methyl ester (50 mg, 0.0903 mmol) in ethanol (0.6 mL) was added dropwise over 20 minutes via a gastight syringe, an aqueous solution of 0.2N sodium hydroxide (0.452 mL) in ethanol (2 mL). After 1 hr, the reaction mixture was diluted with ethyl acetate and acidified with 5% citric acid to pH 3–4. After separation of the organic layer, the aqueous phase was re-extracted with ethyl-acetate (3x). The combined organic layers were washed with water and saturated salt solution and dried over anhydrous magnesium sulfate. The mixture was filtered and the solvents removed by rotoevaporation. The crude product was purified via a Chromatotron (1000μ plate, gradient elution using 1–10% methanol/dichloromethane) to afford the title product (25 mg) and recovered starting ester (25 mg).

Mass spectrum (ESI) m/e=539.6 (M+1)$^+$; 400 MHz $^1$H NMR (CD$_3$OD) δ 1.27 (s, 9H), 2.95–3.15 (m, 1H), 3.20–3.40 (m, 1H), 4.55–4.70 (m, 1H), 6.32 (d, J=1.2 Hz, 1H), 6.66 (dd, J=4.7, 2.6 Hz, 1H), 6.86 (br s, 3H), 7.05–7.25 (m, 2H), 7.57 (d, J=3.2 Hz, 1H), 7.78 (s, 1H), 7.94 (br s, 2H).

EXAMPLE 5

N-[N-(3,5-Dichlorobenznesulfonyl)pyrrole-2-carbonyl]-(L)-O-benzyl-tyrosine

Step A: N-[N-(3,5-Dichlorobenznesulfonyl)pyrrole-2-carbonyl]-(L)-tyrosine, methyl ester At 0° C., to a stirred solution of N-[(N-3,5-dichlorobenznesulfonyl-2-carbonyl)pyrrole]-(L)-O-tert-butyl-tyrosine, methyl ester (obtained from Example 4, Step A) (0.344 g, 0.622 mmol) in dichloromethane (1 mL) was added dropwise a 1:1 (v/v) solution of trifluoroacetic acid/dichloromethane (0.958 mL). The reaction mixture was allowed to warm up to room temperature slowly and stirred for a total of 4 hr. The excess trifluoroacetic acid was removed by a stream of nitrogen gas and the residue was coevaporated with dichloromethane and then pumped under reduced pressure overnight to give the title compound (316 mg, 95%) as a foam, homogeneous by TLC (1/1 hexane/ethyl acetate). This material was used in the subsequent reaction without further purification.

Mass spectrum (ESI) m/e=497.5 (M+1)$^+$; 400 MHz $^1$H NMR (CDCl$_3$) δ 1.9–2.7 (br s, 1H), 3.10–3.15 (m, 2H), 3.74 (s, 3H), 4.90 (m, 1H), 6.28 (t, J=3.4 Hz, 1H), 6.47 (d, J=7.8 Hz, 1H), 6.60 (dd, J=3.5, 1.7 Hz, 1H), 6.72 (d, J=8.6 Hz, 2H), 6.96 (d, J=8.6 Hz, 2H), 7.45 (dd, J=3.3, 1.6 Hz, 1H), 7.56 (t, J=1.8 Hz, 1H), 7.89 (d, J=1.8 Hz, 2H).

Step B: N-[N-(3,5-Dichlorobenzenesulfonyl)pyrrole-2-carbonyl]-(L)-O-benzyl-tyrosine, methyl ester A mixture of N-[N-(3,5-dichlorobenzenesulfonyl)pyrrole-2-carbonyl]-(L)-tyrosine, methyl ester (90 mg, 0.18 mmol), benzyl bromide (123 mg, 0.72 mmol), powdered anhydrous potassium carbonate (150 mg; 1.09 mmol) in dimethylformamide (3 mL) was stirred overnight at 40° C. Acetic acid was added to pH 4–5 and the reaction mixture extracted with ethyl acetate (4x). The combined organic layers were washed with water and saturated salt solution and dried over anhydrous magnesium sulfate. The mixture was filtered and the solvents were removed rotoevaporation. The crude product was purified via Chromatotron (gradient elution using hexane/ethyl acetate) to afford the title compound (12.4 mg), homogeneous by TLC in 1/1 hexane/ethyl acetate), and recovered starting material (46 mg).

Mass spectrum (ESI) m/e=587.4 (M+1)$^+$; 400 MHz $^1$H NMR (CDCl$_3$) δ 3.08–3.20 (m, 2H), 3.74 (s, 3H), 4.88–4.96 (m, 1H), 5.01 (s, 2H), 6.27 (d, J=3.4 Hz, 1H), 6.44 (d, J=7.9 Hz, 1H), 6.58 (dd, J=3.6, 1.8 Hz, 1H), 6.88 (d, J=8.6 Hz, 2H), 7.02 (d, J=8.6 Hz, 2H), 7.25–7.46 (m, 6H), 7.56 (d, J=2.0 Hz, 1H), 7.91 (d, J=1.8 Hz, 2H).

Step C: N-[N-(3,5-Dichlorobenznesulfonyl)pyrrole-2-carbonyl]-(L)-O-benzyl-tyrosine To a stirred solution of N-[N-(3,5-dichlorobenznesulfonyl)pyrrole-2-carbonyl]-(L)-O-benzyl-tyrosine, methyl ester (12.4 mg, 0.021 mmol), in ethanol (0.5 mL) at 0° C., was added dropwise over 10 minutes via a gastight syringe a solution of aqueous 0.2N sodium hydroxide (0.106 mL) in ethanol (1 mL). The reaction mixture was slowly warmed up to room temperature. After stirring for 6.5 hr, the reaction mixture was diluted with ethyl acetate and water in the cold, and acidified with 1.0N acetic acid to pH 4–5. After separation of the layers, the aqueous phase was re-extracted with ethyl acetate (3×). The combined organic layers were washed with water and saturated salt solution and dried over anhydrous magnesium sulfate. The mixture was filtered and the solvent removed by rotoevaporation. The crude product was purified via a Chromatotron (1000μ plate, gradient elution using 1–10% methanol/dichloromethane) to afford the title product (1.2 mg).

Mass spectrum (ESI) m/e=590.41 (M+NH$_4$)$^+$; 500 MHz $^1$H NMR (CD$_3$OD) δ 3.01 (dd, J=13.9, 7.7 Hz, 1H), 3.3.18 (dd, J=13.9, 5.3 Hz, 1H), 4.62 (m, 1H), 5.02 (s, 2H), 6.33 (d, J=3.4 Hz, 1H), 6.67 (dd, J=3.4, 1.6 Hz, 1H), 6.87 (d, J=8.4 Hz, 2H), 7.13 (d, J=8.4 Hz, 2H), 7.25–7.44 (m, 5H), 7.57 (dd, J=3.2, 1.6 Hz, 1H), 7.75 (d, J=1.8 Hz, 1H), 7.92 (d, J=1.8 Hz, 2H).

EXAMPLE 6

N-[N-(3,5-Dichlorobenzenesulfonyl)pyrrole-2-carbonyl]-(L)-(4-(2-methoxyphenyl)phenylalanine Step A: N-Butoxycarbonyl-L-4-iodophenylalanine tert-butyl ester To a solution of N-butoxycarbonyl-(L)-4-iodophenylalanine (1.00 g, 2.56 mmol) in anhydrous dichloromethane (5 mL) and anhydrous dimethylformamide (0.5 mL) at room temperature was added anhydrous cyclohexane (14 mL). To this clear solution with vigorous stirring was added tert-butyl 2,2,2-trichloroacetimidate (0.482 mL, 0.588 g, 2.69 mmol) followed by dropwise addition of boron trifluoride diethyl etherate (75 mL). After stirring at room temperature for 2 hr, additional tert-butyl 2,2,2-trichloroacetimidate (0.482 mL, 0.588 g, 2.69 mmol) and boron trifluoride diethyl etherate (75 mL) were added to the reaction mixture and stirring was continued overnight at room temperature. The reaction mixture was filtered through a pad of celite, and the residue was washed with ether. The solvents were removed by rotoevaporation and the crude product was purified by flash column chromatography through silica gel eluted with 2–6% ethyl acetate in hexane to afford the title compound (840 mg, 73% yield) as an oil, homogeneous by TLC (6/1 hexane/Ethyl acetate).

Mass spectrum (ESI) m/e=448.5 (M+1); 400 MHz $^1$H NMR (CDCl$_3$) δ 1.39 (s, 9H), 1.40(s, 9H), 2.90–3.18 (m, 2H), 4.40 (dd, J=7.8, 3.6 Hz, 1H), 4.95–5.02 (br d, 1H), 6.89(d, J=8.4 Hz, 2H), 7.58 (d, J=8.4 Hz, 2H).

Step B: (L)-4-iodophenylalanine, tert-butyl ester hydrochloride

N-butoxycarbonyl-(L)-4-iodophenylalanine (723 mg, 1.62 mmol) was dissolved in anhydrous ethyl acetate (0.5 mL) at room temperature and then cooled to 0° C. 1N Hydrochloric acid in ethyl acetate (4.0 mL) was added dropwise and the ice bath removed 30 minutes after completion of the addition. The reaction mixture was allowed to stir at room temperature overnight. Additional 1N Hydrochloric acid in ethyl acetate (4.0 mL) was added and the mixture allowed to stir for another 24 hr. Solvents were removed rotoevaporation and the resulting white powder was dried overnight under reduced pressure at room temperature to afford the title compound (610 mg, 98% yield), homogeneous by TLC (10% methanol/dichloromethane) which was used in subsequent reactions without further purification.

Mass spectrum (ESI) m/e=348.2 (M+1); 400 MHz $^1$H NMR (CD$_3$OD) δ 1.41(s, 9H),3.11 (d, J=6.6 Hz, 2H), 4.15 (t, J=6.6 Hz, 1H), 7.07 (d, J=7.9 Hz, 2H), 7.71 (d, J=7.9 Hz, 2H).

Step C: N-[N-(3,5-Dichlorobenznesulfonyl)pyrrole-2-carbonyl]-(L)-4-iodophenylalanine, tert-butyl ester The title compound was prepared from (N-3,5-dichlorobenzenesulfonyl)pyrrole-2-carboxylic acid (obtained from Example 1, Step C) and (L)-4-iodophenylalanine, tert-butyl ester hydrochloride (obtained from Step B) according to the procedure of Example 1, Step D. A 72% yield of the title compound was obtained after chromatographic purification.

Mass spectrum (ESI) m/e=649.3(M+1); 500 MHz $^1$H NMR (CDCl$_3$) δ 1.46 (s, 9H), 3.10–3.20 (m, 2H), 4.81 (dd, J=12.1, 5.9 Hz, 1H), 6.32 (t, J=3.2 Hz, 1H), 6.52 (d, J=7.3 Hz, 1H), 6.64 (dd, J=3.4, 1.8 Hz, 1H), 6.95 (d, J=8.0 Hz, 2H), 7.49 (dd, J=3.0, 1.4 Hz, 1H), 7.60 (m, 1H), 7.62 (d, J=8.1 Hz, 2H), 7.95 (d, J=1.6 Hz, 2H).

Step D: N-[N-(3,5-Dichlorobenznesulfonyl)pyrrole-2-carbonyl]-(L)-4-(2-methoxyphenyl)phenylalanine, tert-butyl ester A mixture of 2-methoxybenzene boronic acid (13 mg, 0.085 mmol) and 2.0N aqueous sodium carbonate (89 μL) in anhydrous ethanol (0.13 mL) was stirred vigorously at room temperature for 30 minutes. More anhydrous ethanol (0.12 mL) was added and stirring continued for 5 min. To this slurry was added of N-[N-(3,5-dichlorobenzenesulfonyl) pyrrole-2-carbonyl]-(L)-4-iodophenylalanine, tert-butyl ester (obtained from Step C) (46 mg, 0.071 mmol). This mixture was degassed and filled with dry nitrogen three times. Tetrakis(triphenylphosphine)palladium(0) (8.2 mg, 0.0071 mmol) was added and the flask degassed/filled with dry nitrogen twice. The reaction mixture was heated in an oil bath to 60° C. for 6 hr. After cooling to room temperature, the solvents were removed by rotoevaporation and the residue was dissolved in 5% aqueous sodium carbonate, then extracted with ethyl acetate (3×). The combined organic layers were washed with water and saturated salt solution and dried over anhydrous sodium sulfate. The mixture was filtered and the solvents removed from the filtrate by rotoevaporation. The crude product was purified by flash column chromatography through silica gel eluted with 2–6% ethyl acetate in hexane to afford the title compound (40 mg, 89% yield) as an off-white foam.

Mass spectrum (ESI) m/e=646.6 (M+NH$_4$). 400 MHz $^1$H NMR (CDCl$_3$) δ 1.42 (s, 9H), 3.19 (t, J=5.1 Hz, 2H), 3.77 (s, 3H), 4.80–4.88 (m, 1H), 6.27 (t, J=3.5 Hz, 1H), 6.52 (d, J=7.4 Hz, 1H), 6.61 (dd, J=3.6, 1.8 Hz, 1H), 6.95 (d, J=7.9 Hz, 1H), 7.00 (dt, J=7.4, 1.0 Hz, 1H), 7.19 (d, J=8.3 Hz, 2H), 7.28 (d, J=8.3 Hz, 2H), 7.42–7.46 (m, 3H), 7.55 (t, J=1.8 Hz, 1H), 7.94 (d, J=1.8 Hz, 2H).

Step E: N-[N-(3,5-Dichlorobenzenesulfonyl)pyrrole-2-carbonyl]-(L)-4-(2-methyoxyphenyl)phenylalanine N-[N-(3,5-Dichlorobenznesulfonyl)pyrrole-2-carbonyl]-(L)-4-(2-methoxyphenyl)phenylalanine, tert-butyl ester (obtained from Step D) was treated with trifluoroacetic acid/dichloromethane according to Example 1, Step E to afford the title compound in 58% yield as a white foam, homogeneous by TLC (10% methanol/dichloromethane).

Mass spectrum (ESI) m/e=573.4 (M+1). 500 MHz $^1$H NMR (CD$_3$OD) δ 3.16(m, 1H), 3.28 (m, 1H), 3.69 (s, 3H), 4.60 (m, 1H), 6.26 (t, J=3.5 Hz, 1H), 6.64 (dd, J=3.7, 1.7 Hz, 1H), 6.92 (dt, J=7.3, 0.7 Hz, 1H), 6.95 (d, J=8.1 Hz, 1H), 7.16 (dd, J=7.5, 1.6 Hz, 1H), 7.22 (d, J=8.0 Hz, 2H), 7.24 (m, 1H), 7.33 (d, J=8.0 Hz, 2H), 7.50 (dd, J=3.1, 1.6 Hz, 1H) 7.64 (t, J=1.8 Hz, 1H), 7.91 (d, J=1.8 Hz, 2H).

EXAMPLE 7

N-[N-(3,5-Dichlorobenzenesulfonyl)pyrrole-2-carbonyl]-(L)-(4-(3-methoxyphenyl)phenylalanine The title compound was prepared as described for N-[N-(3,5-dichlorobenzenesulfonyl)pyrrole-2-carbonyl]-(L)-(4-

(2-methyoxyphenyl)phenylalanine in Example 5 except that 3-methoxybenzene boronic acid was used instead of 2-methoxybenzene boronic acid. The title compound was homogeneous by TLC (10% methanol/dichloromethane) and obtained in a 26% yield.

Mass spectrum (ESI) m/e=573.4 (M+1). 500 MHz $^1$H NMR (CD$_3$OD) δ 3.12(dd, J=13.7, 7.1 Hz, 1H), 3.29 (dd, J=13.9, 5.0 Hz, 1H), 3.80 (s, 3H), 4.62 (m, 1H), 6.30 (t, J=3.2 Hz, 1H), 6.69 (d, J=2.5 Hz, 1H), 6.84 (dd, J=8.2, 2.7 Hz, 1H), 7.05 (br s, 1H), 7.09 (d, J=7.8 Hz, 1H), 7.26 (m, 2H), 7.27 (d, J=8.0 Hz, 2H), 7.44 (d, J=8.0 Hz, 2H), 7.54 (br s, 1H) 7.68 (t, J=1.0 Hz, 1H), 7.91 (d, J=1.0 Hz, 2H).

EXAMPLE 8

N-[N-(3,5-Dichlorobenznesulfonyl)pyrrole-2-carbonyl]-(L)-(4-(2-cyanophenyl)phenylalanine Step A: N-[N-(3,5-Dichlorobenznesulfonyl)pyrrole-2-carbonyl]-(L)-4-(trimethyltin)phenylalanine, tert-butyl ester A mixture of N-[N-(3,5-dichlorobenznesulfonyl)pyrrole-2-carbonyl]-(L)-4-iodophenylalanine, tert-butyl ester (obtained from Example 5 Step C) (400 mg, 0.616 mmol), dry 1,4-dioxane (4 mL), lithium chloride (29 mg, 0.68 mmol), and triphenylphosphine (3.2 mg, 0.012 mmol) at room temperature was degassed and filled with dry nitrogen (4×). Under dry nitrogen, hexamethylditin (166 μL, 0.862 mmol) was added and the mixture was again degassed and filled with dry nitrogen (3×) before tetrakis (triphenylphonphine)palladium(0) (50 mg, 0.043 mmol) was added. The resulting yellow reaction mixture was stirred in an oil bath at 95° C. and for 2.5 hr. After cooling to room temperature, the reaction mixture was dissolved in ethyl acetate (30 mL) and washed with 5% sodium bicarbonate solution (2×5 mL) and saturated salt solution (2×5 mL), and dried over anhydrous magnesium sulfate. The mixture was filtered and the solvent was removed by rotoevaporation. The crude product was purified by flash column chromatography through silica gel eluted with 2–6% ethyl acetate in hexane to afford the title compound (344 mg, 81% yield) as a wet yellow solid, homogeneous by TLC (5/1 hexane/Ethyl acetate) after pumping in vacuo overnight.

Mass spectrum (ESI) m/e=687.5 (M+1). 400 MHz $^1$H NMR (CDCl$_3$) δ 0.25 (s, 9H), 1.42 (s, 9H), 3.13 (d, J=5.5 Hz, 2H), 4.79 (m, 1H), 6.27 (t, J=3.5 Hz, 1H), 6.46 (d, J=7.7 Hz, 1H), 6.59 (dd, J=3.4, 1.5 Hz, 1H), 7.12 (d, J=7.9 Hz, 2H), 7.38 (d, J=8.0 Hz, 2H), 7.45 (dd, J=3.2, 1.8 Hz, 1H), 7.55 (d, J=1.8 Hz, 1H), 7.92 (d, J=1.8 Hz, 2H).

Step B: N-[N-(3,5-Dichlorobenzenesulfonyl)pyrrole-2-carbonyl]-(L)-4-(2-cyanophenyl)phenylalanine, tert-butyl ester A solution of N-[N-(3,5-Dichlorobenzenesulfonyl)pyrrole-2-carbonyl]-(L)-4-(trimethyltin)phenylalanine, tert-butyl ester (obtained from Step A) (100 mg, 0.146 mmol) and 2-bromobenzonitrile (40 mg, 0.219 mmol) in anhydrous toluene (4 mL) was degassed and filled with dry nitrogen (4×) before dichlorobis(triphenylphonpine)palladium(II) (4.10 mg, 0.0584 mmol) was added. The resulting mixture was again degassed and filled with dry nitrogen (2×) before being placed in a pre-heated oil bath at 100° C. for 4 hr. After cooling to room temperature, the reaction mixture was diluted with ethyl acetate and washed with 5% sodium bicarbonate solution (2×). The combined organic layers were washed with saturated salt solution (2×), and dried over anhydrous sodium sulfate. The mixture was filtered and the solvents removed by rotoevaporation. The crude product was purified by flash column chromatography through silica gel eluted with 2–6& ethyl acetate in hexane to afford the title compound (75 mg, 82% yield) as a white foam, homogenous by TLC (2/1 hexane/ethyl acetate);

Mass spectrum (ESI) m/e=641.5 (M+NH$_4$). 400 MHz $^1$H NMR (CDCl$_3$) δ 1.42 (s, 9H), 3.23 (d, J=5.8 Hz, 2H), 4.82–4.90 (m, 1H), 6.28 (t, J=3.5 Hz, 1H), 6.57 (d, J=7.4 Hz, 1H), 6.63 (dd, J=3.6, 1.8 Hz, 1H), 7.29 (d, J=8.2 Hz, 2H), 7.41 (dt, J=7.6, 1.2 Hz, 1H), 7.45 (dd, J=3.3, 1.7 Hz, 1H), 7.48 (d, J=8.2 Hz, 2H), 7.49 (m, 1H), 7.56 (t, J=1.8 Hz, 1H), 7.60 (dt, J=7.7, 1.4 Hz, 1H), 7.74 (dd, J=7.7, 1.4 Hz, 1H), 7.93 (d, J=1.8 Hz, 2H).

Step C: N-[N-(3,5-Dichlorobenznesulfonyl)pyrrole-2-carbonyl]-(L)-(4-(2-cyanophenyl)phenylalanine N-[N-(3,5-Dichlorobenznesulfonyl)pyrrole-2-carbonyl]-(L)-4-(2-cyanophenyl)phenylalanine, tert-butyl ester (obtained from Step B) was treated with trifluoroacetic acid/dichloromethane according to Example 1, Step E to afford the title compound in 91% yield as a white foam, homogeneous by TLC (10% methanol/dichloromethane).

Mass spectrum (ESI) m/e=585.4 (M+NH$_4$). 400 MHz $^1$H NMR (CD$_3$OD) δ 3.18 (dd, J=13.7, 7.0 Hz, 1H), 3.33 (m, 1H), 4.62 (m, 1H), 6.31 (t, J=3.4 Hz, 1H), 6.68 (dd, J=3.5, 1.7 Hz, 1H), 7.37 (d, J=8.3 Hz, 1H), 7.38 (m, 1H), 7.45 (d, J=8.3 Hz, 2H), 7.48 (dt, J=7.6, 1.2 Hz, 1H), 7.51 (d, J=7,6 Hz, 1H), 7.56 (dd, J=3.2, 1.7 Hz, 1H), 7.67 (dt, J=7.7, 1.3 Hz, 1H), 7.75 (t, J=2.0 Hz, 1H), 7.78 (d, J=7.7, 1H), 7.95 (d, J=2.0 Hz, 2H).

EXAMPLE 9

N-[N-(3,5-Dichlorobenznesulfonyl)pyrrole-2-carbonyl]-(L)-(4-(3-cyanophenyl)phenylalanine The title compound was prepared as described for N-[N-(3,5-dichlorobenznesulfonyl)pyrrole-2-carbonyl]-(L)-(4-(2-cyanophenyl)phenylalanine in Example 7 except that 3-bromobenzonitrile was used instead of 2-bromobenzonitrile. The title compound was homogeneous by TLC (10% methanol/dichloromethane) and obtained in a 91% yield.

Mass spectrum (ESI) m/e=567.5 (M+1). 400 MHz $^1$H NMR (CD$_3$OD) δ 3.15 (dd, J=13.5, 6.8 Hz, 1H), 3.33 (m, 1H), 4.65 (m, 1H), 6.33 (t, J=3.5 Hz, 1H), 6.71 (dd, J=3.7, 1.8 Hz, 1H), 7.35 (d, J=8.3 Hz, 1H), 7.53 (d, J=8.3 Hz, 2H), 7.56–7.60 (m, 2H), 7.64 (td, J=7.8, 1.4 Hz, 1H), 7.71 (t, J=2.0 Hz, 1H), 7.87 (td, J=7.9, 1.3 Hz, 1H), 7.90 (m, 2H), 7.91 (d, J=2.0 Hz, 2H).

EXAMPLE 10

N-[N-(3,5-Dichlorobenzenesulfonyl)pyrrole-2-carbonyl]-(L)-(4-(2-propyloxyphenyl)phenylalanine The title compound was prepared as described for N-[N-(3,5-dichlorobenznesulfonyl)pyrrole-2-carbonyl]-(L)-(4-(2-cyanophenyl)phenylalanine in Example 7 except that 2-propxybromobenzene (obtained from the corresponding phenol by treatment with potassium carbonate and iodopropane) was used instead of 2-bromobenzonitrile. The title compound was homogeneous by TLC (10% methanol/dichloromethane) and obtained in a 37% yield.

Mass spectrum (ESI) m/e=601 (M+1). 500 MHz $^1$H NMR (CD$_3$OD) δ 0.87 (t, J=7.3 Hz, 3H), 1.63 (m, 2H), 3.15 (m, 2H), 3.86 (t, J=6.4 Hz, 2H), 4.68 (dd, J=5.0, 7.5 Hz, 1H), 6.30 (m, 1H), 6.64 (m, 1H), 6.92 (m, 1H) 7.18–7.44 (m, 5H), 7.45–7.57 (m, 2H), 7.70 (m, 1H), 7.87 (td, J=7.9, 1.3 Hz, 1H), 7.91 (m, 1H), 7.93 (d, J=1.8 Hz, 2H).

EXAMPLE 11

N-[N-(3,5-Dichlorobenzenesulfonyl)pyrrole-2-carbonyl]-(L)-(4-(2-tetrazolylphenyl)phenylalanine Step A: N-[N-(3,5-Dichlorobenznesulfonyl)pyrrole-2-carbonyl]-(L)-(4(2-tetrazolylphenyl)phenylalanine t-butyl ester N-[N-(3,5-Dichlorobenznesulfonyl)pyrrole-2-carbonyl]-(L)-(4-(2-cyanophenyl)phenylalanine t-butyl ester (44 mg, 0.070 mmoL, obtained from Example 8, Step B) was dissolved in toluene and 66 mg (0.32 mmol) of trimethyltin azide was added. The mixture was stirred and refluxed for 36 h. TLC (2:1 hexane/ethyl acetate) indicated disappearance of most of starting material. After being cooled to room temperature, volatiles were removed and the residue was triburated with ether. The ether insoluble portion was taken up in 3 mL of methanol and stirred with 1 g slica gel overnight at room temperature. The methanol was carefully removed and the crude product thus obtained was flash chromatographed over 10 mL silicq gel, (eluting with 1–2–5–7–10% methanol/dichloromethane) to give 12 mg of a gum, homogeneous by TLC (10% methanol/methylene chloride)

Mass spectrum (ESI) m/e=667.0 (M+H). 400 MHz $^1$H NMR (CDCl$_3$) δ 1.49 (s, 9H), 2.93 (dd, J=13.6, 7.8 Hz), 1H), 3.30 (m, 1H), 4.89–4.95 (m, 1H), 6.31 (m, 1H), 6.69 (m, 1H), 6.77 (d, J=8.0 Hz, 1H), 7.13 (m, 2H), 7.24 (m, 2H), 7.40–7.60 (m, 4H), 7.82 (s, 2H), 8.06–8.18 (m, 1H).

Step B: N-[N-(3,5-Dichlorobenznesulfonyl)pyrrole-2-carbonyl]-(L)-(4-(2-tetrazolylphenyl)phenylalanine N-[N-(3,5-Dichlorobenznesulfonyl)pyrrole-2-carbonyl]-(L)-(4-(2-tetrazolylphenyl)phenylalanine t-butyl ester (obtained from Step A) was treated with trifluoroacetic acid/dichloromethane according to Example 1, Step E to afford the title compound in 50% yield as a white foam, homogeneous by TLC (10% methanol/dichloromethane).

Mass spectrum (ESI) m/e=611 (M+H). 500 MHz $^1$H NMR (CD$_3$OD) δ 3.07 (dd, J=13,8.7 Hz, 1H), 3.27 (m, 1H), 4.72 (dd, J=5.1, 8.7 Hz, 1H), 6.37 (t, J=3.4 Hz, 1H), 6.64 (dd, J=3.7, 1.9 Hz, 1H), 7.04 (d, J=8.1 Hz, 2H), 7.20 (d, J=8.1 Hz, 2H), 7.40–7.80 (m, 5H), 7.94 (d, J=1.8 Hz, 2H).

EXAMPLE 12

N-[N-(3,5-Dichlorobenzenesulfonyl)pyrrole-2-carbonyl]-(L)-(4-(2-methylthiophenyl)phenylalanine The title compound was prepared as described for N-[N-(3,5-dichlorobenznesulfonyl)pyrrole-2-carbonyl]-(L)-(4-(2-cyanophenyl)phenylalanine in Example 7 except that 2-bromothioanisole) was used instead of 2-bromobenzonitrile. The title compound was homogeneous by TLC (10% methanol/dichloromethane) and obtained in a 45% yield.

Mass spectrum (ESI) m/e=606 (M+NH$_4$). 500 MHz $^1$H NMR (CD$_3$OD) δ 2.27 (s, 3H), 3.15 (dd, J=13.7, 7.1 Hz, 1H); 3.35 (m, 1H), 4.63 (m, 1H), 6.32 (t, J=3.5 Hz, 1H), 6.67 (m, 1H), 7.0–7.2 (m, 3H), 7.2–7.5 (m, 5H), 7.54 (t, J=1.4 Hz, 1H), 7.75 (m, 1H), 7.95 (d, J=1.8 Hz, 2H).

EXAMPLE 13

N-[N-(3,5-Dichlorobenznesulfonyl)pyrrole-2-carbonyl]-(L)-(4-(2-methylsulfonylphenyl) phenylalanine Step A: N-[N-(3,5-Dichlorobenznesulfonyl)pyrrole-2-carbonyl]-(L)-(4-(2-methylthiophenyl)phenylalanine, t-butyl ester The title compound was prepared as described for N-[N-(3,5-dichlorobenznesulfonyl)pyrrole-2-carbonyl]-(L)-(4-(2-cyanophenyl)phenylalanine t-butyl ester in Example 7 Step A except that 2-bromothioanisole) was used instead of 2-bromobenzonitrile. The title compound was homogeneous by TLC (5:1 hexane/ethyl acetate) and obtained in a 5% yield.

Mass spectrum (ESI) m/e=645 (M+H). 500 MHz $^1$H NMR (CDCl$_3$) δ 1.43 (s, 9H), 2.32 (s, 3H), 3.22 (d, J=5.8 Hz, 2H), 4.84 (dd, J=1.7, 5.8 Hz, 1H), 6.27 (t, J=3.4 Hz, 1H), 6.53 (d, J=7.6 Hz, 1H), 6.61 (dd J=1.7,3.6 Hz, 1H), 7.15–7.4 (m, 8H), 7.45 (dd, J=1.7, 3.3 Hz, 1H), 7.55 (t, J=2.1 Hz, 1H), 7.94 (d, J=1.8 Hz, 2H).

Step B: N-[N-(3,5-Dichlorobenznesulfonyl)pyrrole-2-carbonyl]-(L)-(4-(2-methylsulfonylphenyl)phenylalanine t-butyl ester N-[N-(3,5-Dichlorobenznesulfonyl)pyrrole-2-carbonyl]-(L)-(4-(2-methylthiophenyl)phenylalanine t-butyl ester (15 mg, 0.023 mmol) was dissolved in 0.100 mL of dichloromethane and cooled to 0° C. m-Chloroperbenzoic acid (8.6 mg, 0.046 mmoL) was added and the ice-bath was removed. After being stirred at room temperature for 3 h, the reaction mixture was diluted with methylene chloride and washed with 5% aqueous sodium bicarbonate. The phases were separated and the aqueous phase was reextracted with methylene chloride twice more. The organic layers were combined and washed with brine and dried over anhydrous sodium sulfate. The residue obtained after filtration and removal of volatiles was flashed chromatographed to give 7 mg (44%) of the desired product, cleanly. Homogeneous by TLC (2:1 hexanelethyl acetate)

Mass spectrum (ESI) m/e=674.3 (M+NH$_4$). 500 MHz $^1$H NMR (CDCl$_3$) δ 1.49 (s, 9H), 2.58 (s, 3H), 3.21 (dd, J=5.3, 14 Hz, 1H), 3.32 (dd, J=5.9, 14 Hz, 1H), 4.89 (dd, J=5.7, 13 Hz, 1H), 6.32 (t, J=3.4 Hz, 1H), 6.65 (d, J=7.3 Hz, 1H), 6.69 (dd J=1.6,3.4 Hz, 1H), 7.25–7.65 (m, 5H), 7.65–7.70 (m, 3H), 7.97 (d, J=1.9 Hz, 2H), 8.24 (dd, J=1.1, 8.0 Hz, 1H).

Step C: N-[N-(3,5-Dichlorobenznesulfonyl)pyrrole-2-carbonyl]-(L)-(4-(2-methylsulfonylphenyl)phenylalanine N-[N-(3,5-Dichlorobenznesulfonyl)pyrrole-2-carbonyl]-(L)-(4-(2-methylsulfonylphenyl)phenylalanine t-butyl ester (obtained from Step B) was treated with trifluoroacetic acid/dichloromethane according to Example 1, Step E to afford the title compound in 65% yield as a white foam, homogeneous by TLC (10% methanol/dichloromethane).

Mass spectrum (ESI) m/e=638 (M+NH$_4$). 500 MHz $^1$H NMR (CD$_3$OD) δ 2.49 (s, 3H), 3.14 (dd, J=13.7, 5.7 Hz, 1H), 3.36 (m, 1H), 4.65 (m, 1H), 6.34 (t, J=3.4 Hz, 1H), 6.73 (dd, J=3.7, 1.7 Hz, 1H), 7.30–7.50 (m, 5H), 7.55–7.95 (m, 4H), 7.96 (d, J=1.8 Hz, 2H), 8.12 (dd, J=1.2, 7.9 Hz, 1H).

EXAMPLE 14

N-[N-(3,5-Dichlorobenzenesulfonyl)pyrrole-2-carbonyl]-(L)-tyrosine

Step A: N-[N-(3,5-Dichlorobenzenesulfonyl)pyrrole-2-carbonyl]-(L)-(4-t-butyl)tyrosine t-butyl ester N-[N-(3,5-Dichlorobenznesulfonyl)pyrrole-2-carboxylic acid (obtained from Example 1, Step C) was coupled with tyrosine t-butyl ether t-butyl ester hydrochloride according to the procedure of Example 1, Step D to afford the title compound in 60% yield as a white foam, homogeneous by TLC (4:1 hexane/ethyl acetate).

Mass spectrum (ESI) m/e=612 (M+NH$_4$). 400 MHz $^1$H NMR (CDCl$_3$) δ 1.30 (s, 9H), 1.39 (s, 9H), 3.10 (d, J=5.9 Hz, 2H), 4.76 (dd, J=1.7, 5.9 Hz, 1H), 6.26 (t, J=3.4 Hz, 1H), 6.48 (d, J=7.7 Hz, 1H), 6.57 (dd, J=3.5, 1.5 Hz, 1H), 6.88 (dd, J=6.6, 2.0 Hz, 2H), 7.05 (d, J=8.3 Hz, 2H), 7.44 (dd, J=3.3, 1.4 Hz, 1H), 7.55 (t, J=1.8 Hz, 1H), 7.92 (d, J=1.8 Hz, 2H).

Step B: N-[N-(3,5-Dichlorobenzenesulfonyl)pyrrole-2-carbonyl]-(L)-tyrosine

N-[N-(3,5-Dichlorobenzenesulfonyl)pyrrole-2-carbonyl]-(L)-(4-t-butyl)tyrosine t-butyl ester (obtained from Step A) was treated with trifluoroacetic acid/ dichloromethane according to Example 1, Step E to afford the title compound in 25% yield as an orange solid, homogeneous by TLC (10% methanol/dichloromethane).

Mass spectrum (ESI) m/e=500 (M+NH$_4$). 400 MHz $^1$H NMR (CD$_3$OD) δ 2.97 (dd, J=13, 7.4 Hz, 1H), 3.15 (dd, J=13, 5.3 Hz, 1H), 4.51 (dd, J=7.4, 5.3 Hz, 1H), 6.34 (t, J=3.4 Hz, 1H), 6.66 (m, 3H), 7.04 (m, 2H), 7.58 (dd, J=1.6, 3.3 Hz, 1H), 7.78 (m, 1H), 7.94 (d, J=1.4 Hz, 2H).

EXAMPLE 15

Inhibition of VLA-4 Dependent Adhesion to BSA-CS-1 Conjugate

Step A. Preparation of CS-1 Coated Plates.

Untreated 96 well polystyrene flat bottom plates were coated with bovine serum albumin (BSA; 20 μg/ml) for 2 hours at room temperature and washed twice with phosphate buffered saline (PBS). The albumin coating was next derivatized with 10 μg/ml 3-(2-pyridyldithio) propionic acid N-hydroxysuccinimide ester (SPDP), a heterobifunctional crosslinker, for 30 minutes at room temperature and washed twice with PBS. The CS-1 peptide (Cys-Leu-His-Gly-Pro-Glu-Ile-Leu-Asp-Val-Pro-Ser-Thr), which was synthesized by conventional solid phase chemistry and purified by reverse phase HPLC, was next added to the derivatized BSA at a concentration of 2.5 μg/ml and allowed to react for 2 hours at room temperature. The plates were washed twice with PBS and stored at 4° C.

Step B. Preparation of Fluorescently Labeled Jurkat Cells.

Jurkat cells, clone E6-1, obtained from the American Type Culture Collection (Rockville, Md.; cat # ATCC TIB-152) were grown and maintained in RPMI-1640 culture medium containing 10% fetal calf serum (FCS), 50 units/ml penicillin, 50 μg/ml streptomycin and 2 mM glutamine. Fluorescence activated cell sorter analysis with specific monoclonal antibodies confirmed that the cells expressed both the α4 and β1 chains of VLA-4. The cells were centrifuged at 400×g for five minutes and washed twice with PBS. The cells were incubated at a concentration of 2×10$^6$ cells/ml in PBS containing a 1 μM concentration of a fluorogenic esterase substrate (2', 7'-bis-(2-carboxyethyl)-5-(and -6)-carboxyfluorescein, acetoxymethyl ester; BCECF-AM; Molecular Probes Inc., Eugene, Oreg.; catalog #B-1150) for 30–60 minutes at 37° C. in a 5% CO$_2$/air incubator. The fluorescently labeled Jurkat cells were washed two times in PBS and resuspended in RPMI containing 0.25% BSA at a final concentration of 2.0×10$^6$ cells/ml.

Step C. Assay Procedure.

Compounds of this invention were prepared in DMSO at 100× the desired final assay concentration. Final concentrations were selected from a range between 0.001 nM-100 μM. Three μL of diluted compound, or vehicle alone, were premixed with 300 μL of cell suspension in 96-well polystyrene plates with round bottom wells. 100 μL aliquots of the cell/compound mixture were then transferred in duplicate to CS-1 coated wells. The cells were next incubated for 30 minutes at room temperature. The non-adherent cells were removed by two gentle washings with PBS. The remaining adherent cells were quantitated by reading the plates on a Cytofluor II fluorescence plate reader (Perseptive Biosystems Inc., Framingham, Mass.; excitation and emission filter settings were 485 nm and 530 nm, respectively). Control wells containing vehicle alone were used to determine the level of cell adhesion corresponding to 0% inhibition. Wells in which cells were treated with a saturating concentration (10 ng/ml) of a neutralizing anti-α4 antibody (HP 2/1; Immunotech, Inc., Westbrook, Me.) were used to determine the level of cell adhesion corresponding to 100% inhibition. Cell adhesion in the presence of HP2/1 was usually less than 5% of that observed in the presence of vehicle alone. Percent inhibition was then calculated for each test well and the IC$_{50}$ was determined from an eight point titration using a validated four parameter fit algorithm.

EXAMPLE 16

Antagonism of VLA-4 Dependent Binding to VCAM-Ig Fusion Protein

Step A. Preparation of VCAM-Ig.

The signal peptide as well as domains 1 and 2 of human VCAM (GenBank Accession no. M30257) were amplified by PCR using the human VCAM cDNA (R & D Systems) as template and the following primer sequences: 3'-PCR primer:5'-AATTATAATTTGATCAACTTAC CTGTCAATTCTTTTACAGCCTGCC-3';
5'-PCR primer:
5'-ATAGGAATTCCAGCTGCCACCATGCCTGGGAAGA TGGTCG-3'.

The 5'-PCR primer contained EcoRI and PvuII restriction sites followed by a Kozak consensus sequence (CCACC) proximal to the initiator methionine ATG. The 3'-PCR primer contained a BclI site and a splice donor sequence. PCR was performed for 30 cycles using the following parameters: 1 min. at 94° C., 2 min. at 55° C., and 2 min. at 72° C. The amplified region encoded the following sequence of human VCAM-1:
MPGKMVVILGASNILWIMFAASQAFKI-ETTPESRYLQIGDSVSLTC STTGCESPFFSWRTQID-SPLNGKVTNEGTTSTLTMNPVSFGNEHSYLC TAT-CESRKLEKGIQVEIYSFPKDPEIHLSGPLEAGKPITVK CSVADVY PFDRLEIDLLKGDHLMKSQE-FLEDADRKSLETKSLEVTFTPVIEDIGK VLVCRAKL-HIDEMDSVPTVRQAVKEL. The resulting PCR product of 650 bp was digested with EcoRI and BclI and ligated to expression vector pIg-Tail (R & D Systems, Minneapolis, Minn.) digested with EcoRI and BamHI. The pIg-Tail vector contains the genomic fragment which encodes the hinge region, CH2 and CH3 of human IgG1 (GenBank Accession no. Z17370). The DNA sequence of the resulting VCAM fragment was verified using Sequenase (US Biochemical, Cleveland, Ohio). The fragment encoding the entire VCAM-Ig fusion was subsequently excised from pIg-Tail with EcoRI and NotI and ligated to pCI-neo (Promega, Madison, Wis.) digested with EcoRI and NotI. The resulting vector, designated pCI-neo/VCAM-Ig was transfected into CHO-K1 (ATCC CCL 61) cells using calcium-phosphate DNA precipitation (Specialty Media, Lavalette, N.J.). Stable VCAM-Ig producing clones were selected according to standard protocols using 0.2–0.8 mg/ml active G418 (Gibco, Grand Island, N.Y.), expanded, and cell supernatants were screened for their ability to mediate Jurkat adhesion to wells previously coated with 1.5 μg/ml (total protein) goat anti-human IgG (Sigma, St. Louis, Mo.). A positive CHO-K1/VCAM-Ig clone was subsequently adapted to CHO-SFM serum-free media (Gibco) and maintained under selection for stable expression of VCAMI-Ig. VCAM-Ig was purified from crude culture supernatants by affinity chromatography on Protein A/G Sepharose (Pierce, Rockford, Ill.) according to the manufacturer's instructions and desalted into 50 mM sodium phosphate buffer, pH 7.6, by ultrafiltration on a YM-30 membranes (Amicon, Beverly, Mass.).

Step B. Preparation of $^{125}$I-VCAM-Ig

VCAM-Ig was labeled to a specific radioactivity greater that 1000 Ci/mmole with $^{125}$I-Bolton Hunter reagent (New England Nuclear, Boston, Mass.; cat # NEX120-0142) according to the manufacturer's instructions. The labeled protein was separated from unincorporated isotope by means of a calibrated HPLC gel filtration column (G2000SW; 7.5×600 mm; Tosoh, Japan) using uv and radiometric detection.

Step C. VCAM-Ig Binding Assay.

Compounds of this invention were prepared in DMSO at 100× the desired final assay concentration. Final concentrations were selected from a range between 0.001 nM–100 μM. Jurkat cells were centrifuged at 400×g for five minutes and resuspended in binding buffer (25 mM HEPES, 150 mM NaCl, 3 mM KCl, 2 mM glucose, 1 mM $MnCl_2$, 0.1% bovine serum albumin, pH 7.4) without $MnCl_2$. The cells were centrifuged again and resuspended in complete binding buffer. Compounds were assayed in Millipore MHVB multiscreen plates (cat# MHVBN4550, Millipore Corp., Mass.) by making the following additions to duplicate wells: (i) 200 μL of binding buffer; (ii) 20 μL of a working stock of $^{125}$I-VCAM-Ig prepared in binding buffer (final assay concentration £ 100 pM); (iii) 2.5 μL of compound solution or vehicle alone; (iv) and 0.5×10$^6$ cells in a volume of 30 mL. The plates were incubated at room temperature for 30 minutes, filtered on a vacuum box, and washed on the same apparatus by the addition of 100 μL of binding buffer. After insertion of the multiscreen plates into adapter plates (Packard, Meriden, Conn., cat# 6005178), 100 μL of microscint-20 (Packard cat# 6013621) was added to each well. The plates were then sealed, placed on a shaker for 30 seconds, and counted on a Topcount microplate scintillation counter (Packard). Control wells containing vehicle alone were used to determine the level of VCAM-Ig binding corresponding to 0% inhibition. Wells in which cells were treated with a saturating concentration of unlabeled VCAM-Ig (10 nM) were used to determine the level of binding corresponding to 100% inhibition. Binding of $^{125}$I-VCAM-Ig in the presence of 10 nM unlabeled VCAM-Ig was usually less than 5% of that observed in the presence of vehicle alone. Percent inhibition was then calculated for each test well and the $IC_{50}$ was determined from a ten point titration using a validated four parameter fit algorithm. Compounds of Examples 1–8 showed $IC_{50}$ values of less than 10 nM in the inhibition of VCAM-Ig binding to VLA4. $IC_{50}$ values for the inhibition of VCAM-Ig binding to VLA-4 are provided below for representative compounds:

EXAMPLE 17

Antagonism of $α_4β_7$ Dependent Binding to VCAM-Ig Fusion Protein

Step A. $α_4β_7$ Cell line.

RPMI-8866 cells (a human B cell line $α_4^+β_1^-β_7^+$; a gift from Prof. John Wilkins, University of Manitoba, Canada) were grown in RPMI/10% fetal calf serum/100 U penicillin, 100 μg streptomycin/2 mM L-glutamine at 37° C., 5% carbon dioxide. The cells (1.25×10$^6$ cells/well) were pelleted at 1000 rpm for 5 minutes and then washed twice in binding buffer (25 mM Hepes, 150 mM NaCl, 0.1% BSA, 3 mM KCl, 2 mM Glucose, pH 7.4). Cells were then resuspended at 3.3×10$^7$ cells/ml.

Step B. VCAM-Ig Binding Assay $^{125}$I-VCAM-Ig (prepared as above) was diluted in binding buffer to <500 pM VCAM-Ig/10 μl. (i.e. if specific activity VCAN-1-Ig=3.5×10$^6$ cpm/pmole, then 250,000 cpm/well= 7.14×10$^{-14}$ moles VCAM-Ig. The volume of the assay was 150 ul, and the final concentration of VCAM-Ig=476 pM). Compounds of the present invention and serial dilutions were prepared in DMSO. The final amount of DMSO in the assay was kept at 1% when adding 1.5 μl diluted compound to each well. Compounds were assayed in Millipore MHVB multiscreen plates (Cat# MHVBN4550) by making the following sequential additions to duplicate wells: (i) 100 ul/well of binding buffer containing 1.5 mM $Mn^{++}$; (ii) <500 pM/well $^{125}$I-VCAM-Ig; (iii) 1.5 ul/well test compound; (iv) 38 ul/well RPMI-8866 cell suspension (1.25×10$^6$ cells/ well). Control wells were established as follows: (i) total binding=buffer+$^{125}$I-VCAM-Ig+cells; (ii) non-specific binding=buffer+$^{125}$I-VCAM-Ig–cells. Plates were incubated for 45 min. at 25° C. on a plate shaker at 200 rpm. The multiscreen plates were filtered using a Millipore vacuum manifold (Cat. # MAVM 096 01). The plates were washed once with 100 ul/well binding buffer+1 mM $Mn^{++}$. After vacuum filtration, the plates were blotted, the plastic backing was removed and blotted again and allowed to air dry. When the filters were dry, the plates were transferred to Packard adapter plates (Cat# 6005178). Packard Microscint-20 (100 μL/well) (Cat# 6013621) was added and the plates were sealed. The plates were placed on a plate shaker at 500 rpm for 30 seconds and counted on a Packard Topcount. Percent inhibition was then calculated for each test well and the $IC_{50}$ was determined from a ten point titration using a validated four parameter fit algorithm.

What is claimed is:

1. A compound having the formula I:

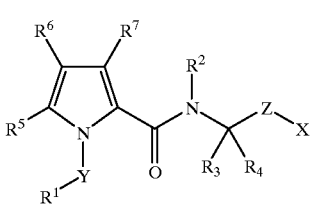

I or a pharmaceutically acceptable salt thereof wherein:
X is 1) —C(O)OR$^d$,
2) —P(O)(OR$^d$)(OR$^e$)
3) —P(O)(R$^d$)(OR$^e$)
4) —S(O)$_m$OR$^d$,
5) —C(O)NR$^d$R$^h$,
Y is 1) —C(O)—,
2) —O—C(O)—,
3) —NR$^e$—C(O)—,
4) —S(O)$_2$—,
5) —P(O)(OR$^4$) or
6) C(O)C(O);
Z is 1) a bond, or
2) —C(R$^8$)(R$^9$)—;
R$^1$ is 1) $C_{1-10}$alkyl,
2) $C_{2-10}$alkenyl,
3) $C_{2-10}$alkynyl,
4) Cy,
5) Cy-$C_{1-10}$alkyl,
6) Cy-$C_{2-10}$alkenyl,
7) Cy-$C_{2-10}$alkynyl,
wherein alkyl, alkenyl, and alkynyl are optionally substituted with one to four substituents independently selected from R$^a$; and Cy is optionally substituted with one to four substituents independently selected from R$^b$;
R$^2$ is 1) hydrogen,
2) $C_{1-10}$alkyl,
3) Cy,
4) Cy-$C_{1-10}$alkyl,
wherein alkyl is optionally substituted with one to four substituents independently selected from R$^a$; and Cy is optionally substituted with one to four substituents independently selected from R$^b$;

$R^3$ is 1) hydrogen,
  2) $C_{1-10}$alkyl,
  3) $C_{2-10}$alkenyl,
  4) $C_{2-10}$alkynyl,
  5) Cy-(Cy)$_p$,
  6) Cy-(Cy)$_p$-$C_{1-10}$alkenyl,
  7) Cy-(Cy)$_p$-$C_{2-10}$alkenyl,
  8) Cy-(Cy)$_p$-$C_{2-10}$alkynyl, alkyl, allenyl and alkynyl are optionally substituted with one to four substituents independently selected from $R^a$; and Cy is optionally substituted with one to four substituents independently selected from $R^b$;

$R^4$ is 1) hydrogen,
  2) $C_{1-10}$alkyl,
  3) $C_{2-10}$alkenyl,
  4) $C_{2-10}$alkynyl,
  5) Cy,
  6) Cy-$C_{1-10}$alkyl, wherein alkyl, alkenyl and alkynyl are optionally substituted with one to four substituents selected from $R^a$, and Cy is optionally substituted with one to four substituents independently selected from $R^b$;

$R^5$, $R^6$, and $R^7$ are each independently
  1) hydrogen, or
  2) a group selected from $R^b$; or $R^5$ and $R^6$ or $R^6$ and $R^7$ and the two adjacent carbon atoms to which they are attached, together form a 5–7 membered saturated or unsaturated monocyclic ring containing zero heteroatoms;

$R^8$ is 1) hydrogen,
  2) a group selected from $R^a$, or
  3) a group selected from $R^1$;

$R^9$ is 1) hydrogen,
  2) $C_{1-10}$alkyl,
  3) $C_{2-10}$alkenyl,
  4) $C_{2-10}$alkynyl,
  5) Cy,
  6) Cy-$C_{1-10}$alkyl, wherein alkyl, alkenyl and alkynyl are optionally substituted with one to four substituents selected from $R^a$, and Cy is optionally substituted with one to four substituents independently selected from $R^b$, $R^a$ is 1) —$CF_3$;
  2) —$OR^d$,
  3) —$NO_2$,
  4) halogen
  5) —$S(O)_mR^d$,
  6) —$SR^d$,
  7) —$S(O)_2OR^d$,
  8) —$S(O)_mNR^dR^e$,
  9) —$NR^dR^e$,
  10) —$O(CR^fR^g)_nNR^dR^e$,
  11) —$C(O)R^d$,
  12) —$CO_2R^d$,
  13) —$CO_2(CR^fR^g)_nCONR^dR^e$,
  14) —$OC(O)R^d$,
  15) —CN,
  16) —$C(O)NR^dR^e$,
  17) —$NR^dC(O)R^e$,
  18) —$OC(O)NR^dR^e$,
  19) —$NR^dC(O)OR^e$, or
  20) —$NR^dC(O)NR^dR^e$;
  21) —$CR^d(N$—$OR^e)$, or
  22) Cy optionally substituted with a group independently selected from $R^c$;

$R^b$ is 1) a group selected from $R^a$,
  2) $C_{1-10}$alkyl,
  3) $C_{2-10}$alkenyl,
  4) $C_{2-10}$alkynyl, or
  5) Cy-$C_{1-10}$alkyl, wherein alkyl, alkenyl, alkynyl, and Cy are optionally substituted with a group independently selected from $R^c$;
substituted with a group independently selected from $R^c$;

$R^c$ is 1) halogen,
  2) amino,
  3) carboxy,
  4) $C_{1-4}$alkyl,
  5) $C_{1-4}$alkoxy,
  6) aryl,
  7) aryl $C_{1-4}$alkyl, or
  8) aryloxy;

$R^d$ and $R^e$ are independently selected from the group consisting of
  1) hydrogen,
  2) $C_{1-10}$alkyl,
  3) $C_{2-10}$alkenyl,
  4) $C_{2-10}$alkaynyl,
  5) Cy, and
  6) Cy $C_{1-10}$alkyl, wherein alkyl, alkenyl, alkynyl and Cy is optionally substituted with one to four substituents independently selected from $R^c$; or $R^d$ and $R^e$ together with the atoms to which they are attached form and;

$R^f$ and $R^g$ are independently selected from hydrogen, $C_{1-10}$alkyl, Cy and Cy $C_{1-10}$alkyl; or $R^f$ and $R^g$ together with the carbon to which they are attached form a ring of 5 to 7 members containing 0 heteroatoms;

$R^h$ is 1) hydrogen,
  2) $C_{1-10}$alkyl,
  3) $C_{2-10}$alkenyl,
  4) $C_{2-10}$alkynyl,
  5) cyano,
  6) aryl,
  7) aryl $C_{1-10}$alkyl, or
  10) —$SO_2R^i$;

wherein alkyl, alkenyl, and alkynyl are optionally substituted with one to four substituents independently selected from $R^a$; and aryl is optionally substituted with one to four substituents independently selected from $R^b$;

$R^i$ is 1) $C_{1-10}$alkyl,
  2) $C_{2-10}$alkenyl,
  3) $C_{2-10}$alkynyl, or
  4) aryl;

wherein alkyl, alkenyl, alkynyl and aryl are each optionally substituted with one to four substituents independently selected from $R^c$;

Cy is cycloalkyl and aryl;
m is an integer from 1 to 2;
n is an integer from 1 to 10; and
p is 0 or 1.

2. A compound of claim 1 wherein $R^1$ is 1) Cy, or
  2) Cy-$C_{1-10}$alkyl wherein alkyl is optionally substituted with one to four substituents independently selected from $R^a$; and Cy is optionally substituted with one to four substituents independently selected from $R^b$.

3. A compound of claim 1 wherein
Y is 1) —C(O)—, or
2) $SO_2$.
4. A compound of claim 1 wherein X is —C(O)$OR^d$.
5. A compound of claim 1 having the formula Ia:

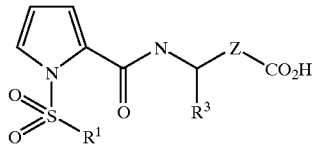

wherein
$R^1$ is aryl optionally substituted with one or two groups independently selected from $R^b$;
$R^3$ is 1) $C_{1-10}$alkyl,
2) Cy-(Cy)$_p$, or
3) Cy-(Cy)$_p$-$C_{1-10}$alkyl,
wherein alkyl is optionally substituted with one to four substituents independently selected from $R^a$; and Cy is optionally substituted with one to four substituents independently selected from $R^b$;
Z is 1) a bond, or
2) —$CH_2$—.
6. A compound of claim 1 selected from the group consisting of:

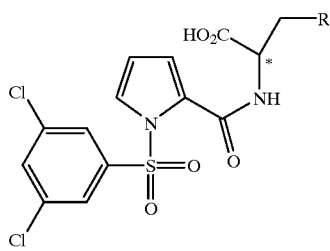

wherein R is phenyl, benzyl, propyl, 4-(t-butoxyphenyl), 4-(benzyloxy)phenyl, 4-(2-methoxyphenyl)phenyl, 4-(3-methoxyphenyl)phenyl, 4-(2-cyanophenyl)phenyl, 4-(3-cyanophenyl)phenyl, 4-(2-propyloxyphenyl)phenyl, 4-(2-methylthiophenyl)phenyl, 4-(2-methylsulfonylphenyl) phenyl, or 4-hydroxyphenyl, and * represents that the stereo configuration is that of an L-amino acid.

7. A method for inhibiting cell adhesion in a mammal which comprises administering to said mammal an effective amount of a compound of claim 1.

8. A method for the treatment of diseases, disorders, conditions or symptoms mediated by cell adhesion in a mammal which comprises administering to said mammal an effective amount of a compound of claim 1.

9. A method for the treatment of asthma in a mammal which comprises administering to said mammal a therapeutically effective amount of a compound of claim 1.

10. A method for the treatment of allergic rhinitis in a mammal which comprises administering to said mammal a therapeutically effective amount of a compound of claim 1.

11. A method for the treatment of multiple sclerosis in a mammal which comprises administering to said mammal a therapeutically effective amount of a compound of claim 1.

12. A method for the treatment of atherosclerosis in a mammal which comprises administering to said mammal a therapeutically effective amount of a compound of claim 1.

13. A method for the treatment of inflammation in a mammal which comprises administering to said mammal an effective amount of a compound of claim 1.

14. A method for the treatment of inflammatory bowel disease in a mammal which comprises administering to said mammal a therapeutically effective amount of a compound of claim 1.

15. A pharmaceutical composition which comprises a compound of claim 1 and a pharmaceutically acceptable carrier thereof.

16. A method for inhibiting cell adhesion in a mammal which comprises administering to said mammal an effective amount of a compound of claim 2.

17. A method for the treatment of diseases, disorders, conditions or symptoms mediated by cell adhesion in a mammal which comprises administering to said mammal an effective amount of a compound of claim 2.

18. A method for the treatment of asthma, allergic rhinitis, multiple sclerosis, atherosclerosis or inflammation in a mammal which comprises administering to said mammal an effective amount of a compound of claim 2.

19. A pharmaceutical composition which comprises a compound of claim 2 and a pharmaceutically acceptable carrier thereof.

* * * * *